(12) United States Patent
Urbanski et al.

(10) Patent No.: US 11,497,549 B2
(45) Date of Patent: Nov. 15, 2022

(54) METHODS AND DEVICES FOR PUNCTURING TISSUE

(71) Applicant: Boston Scientific Medical Device Ltd., Galway (IE)

(72) Inventors: John Paul Urbanski, Toronto (CA); Mahban Samiee-Zafarghandy, Etobicoke (CA); Maria Luk, Kleinburg (CA); James Dylan Klein, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 0 days.

(21) Appl. No.: 17/053,430

(22) PCT Filed: May 7, 2019

(86) PCT No.: PCT/IB2019/053745
§ 371 (c)(1),
(2) Date: Nov. 6, 2020

(87) PCT Pub. No.: WO2019/215618
PCT Pub. Date: Nov. 14, 2019

(65) Prior Publication Data
US 2021/0228268 A1 Jul. 29, 2021

Related U.S. Application Data

(60) Provisional application No. 62/668,396, filed on May 8, 2018.

(51) Int. Cl.
*A61B 18/14* (2006.01)
*A61B 90/00* (2016.01)
*A61B 18/00* (2006.01)

(52) U.S. Cl.
CPC ...... *A61B 18/1487* (2013.01); *A61B 18/1482* (2013.01); *A61B 90/06* (2016.02);
(Continued)

(58) Field of Classification Search
CPC .......... A61M 25/0012; A61M 25/0108; A61M 2205/32
See application file for complete search history.

(56) References Cited

U.S. PATENT DOCUMENTS 6,030,371 A * 2/2000 Pursley ............. A61M 25/0009
427/195
6,270,476 B1 8/2001 Santoianni
(Continued)

FOREIGN PATENT DOCUMENTS

EP 3064246 9/2016
JP 5525513 6/2014
(Continued)

OTHER PUBLICATIONS

Patent Corporation Treaty, International Search Report for PCT Application No. PCT/IB2019/053745, dated Sep. 18, 2019.
(Continued)

*Primary Examiner* — Ronald Hupczey, Jr.
(74) *Attorney, Agent, or Firm* — Dennis Haszko

(57) ABSTRACT

Methods and devices are disclosed for puncturing tissue, comprising a puncture device for puncturing tissue and a supporting member for supporting the puncture device. The puncture device is capable of being insertable within the supporting member and being selectively usable in co-operation therewith during a portion of a procedure for puncturing tissue and wherein the puncture device is usable independently therefrom during another portion of the procedure. The puncture device comprises visual or tactile (Continued)

markers for determining the relative positioning between puncture device and supporting member.

16 Claims, 15 Drawing Sheets

(52) U.S. Cl.
CPC .... *A61B 90/39* (2016.02); *A61B 2018/00077* (2013.01); *A61B 2018/00148* (2013.01); *A61B 2018/00351* (2013.01); *A61B 2018/00577* (2013.01); *A61B 2018/00702* (2013.01); *A61B 2018/00839* (2013.01); *A61B 2018/144* (2013.01); *A61B 2018/1435* (2013.01); *A61B 2090/065* (2016.02); *A61B 2090/376* (2016.02); *A61B 2090/3925* (2016.02); *A61B 2090/3941* (2016.02); *A61B 2090/3966* (2016.02); *A61B 2090/3995* (2016.02); *A61B 2218/002* (2013.01); *A61B 2218/007* (2013.01)

(56) References Cited

U.S. PATENT DOCUMENTS

| | | | |
|---|---|---|---|
| 6,881,214 B2* | 4/2005 | Cosman | A61B 18/1477 606/45 |
| 7,160,292 B2* | 1/2007 | Moorman | A61B 10/0233 600/562 |
| 2001/0051790 A1 | 12/2001 | Parker | |
| 2006/0206131 A1* | 9/2006 | Conquergood | A61B 17/320758 606/180 |
| 2008/0243081 A1 | 10/2008 | Nance et al. | |
| 2010/0249908 A1 | 11/2010 | Chau et al. | |
| 2011/0087261 A1 | 4/2011 | Wittkampf | |
| 2012/0109079 A1 | 5/2012 | Asleson | |
| 2014/0228841 A1 | 8/2014 | Davies et al. | |
| 2014/0275991 A1 | 9/2014 | Potter et al. | |
| 2015/0157353 A1 | 6/2015 | Lenker et al. | |
| 2016/0100860 A1* | 4/2016 | Lenker | A61B 17/3478 604/95.01 |
| 2016/0175009 A1 | 6/2016 | Davies | |
| 2016/0242813 A1 | 8/2016 | Cannon et al. | |
| 2017/0266433 A1 | 9/2017 | Daniels et al. | |
| 2017/0367728 A1* | 12/2017 | Qu | A61B 17/3478 |

FOREIGN PATENT DOCUMENTS

| | | |
|---|---|---|
| JP | 2016-530928 | 10/2016 |
| WO | 2014182969 | 11/2014 |
| WO | 2015019132 | 2/2015 |
| WO | 2016160348 | 10/2016 |

OTHER PUBLICATIONS

Patent Corporation Treaty, Written Opinion for PCT Application No. PCT/IB2019/053745, dated Sep. 18, 2019.

Patent Corporation Treaty, International Search Report for co-pending PCT Application No. PCT/IB2017/056777, dated Mar. 27, 2018.

Patent Corporation Treaty, Written Opinion for co-pending PCT Application No. PCT/IB2017/056777, dated Mar. 27, 2018.

European Search Report of Corresponding European Application, dated Feb. 10, 2022.

Corresponding Japanese Application, Office Action, dated Jun. 14, 2022.

* cited by examiner

METHODS AND DEVICES FOR PUNCTURING TISSUE

TECHNICAL FIELD

The disclosure relates to systems and methods for creating a puncture in tissue. More specifically, the disclosure relates to systems and methods for creating a puncture using an assembly including a puncture device and a supporting member.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
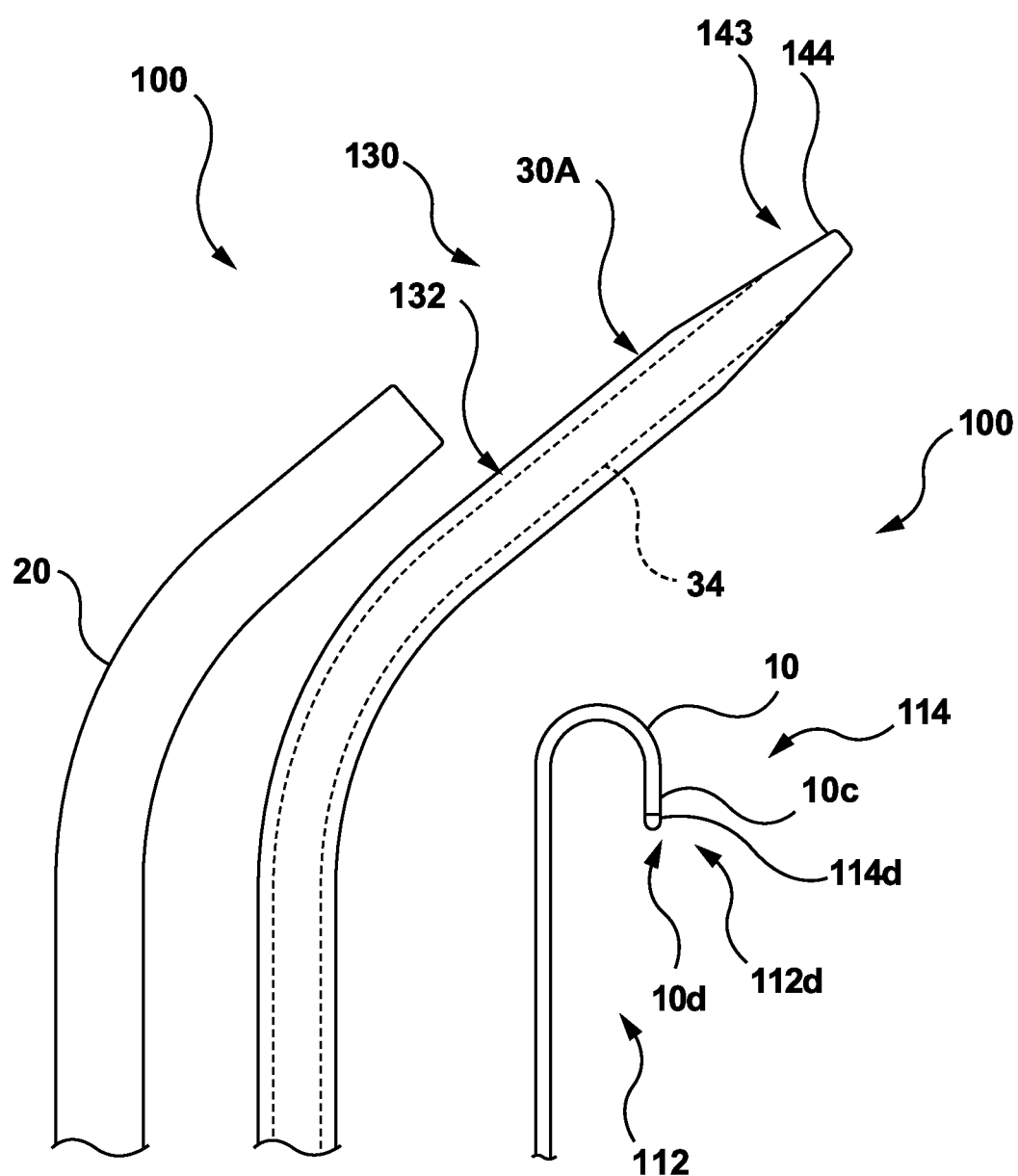
FIGS. 1A and 1B are illustrations of a transseptal assembly in accordance with embodiments of the present invention.

In order to carry out a transseptal procedure, it is necessary to gain access to the heart. Access may be obtained (specifically to the right atrium of the heart) from a superior approach (by gaining access to the heart from an access point above the heart, for example from the jugular vein through the superior vena cava), or alternatively access may be obtained from the femoral or inferior approach (by gaining access to the heart from an access point below the heart, for example from the femoral vein through the inferior vena cava). Once access is obtained into the right atrium, a puncture device is utilized in order to puncture through tissue for example across a septum of the heart to gain access from the right atrium into the left atrium of the heart.

Some conventional transseptal procedures, for example some that use the inferior approach to gain access to the heart, use a needle in order to carry out a transseptal puncture. Certain limitations may be associated with the use of prior art devices for carrying out a transseptal puncture procedure.

During a transseptal puncture procedure, there is a risk of inadvertent puncture of other tissues of the heart before or after the perforation has been created, resulting in general tissue damage within the heart, ancillary device damage (e.g., damage to pacemaker leads located in atrium) or potentially critical complications such as cardiac tamponade. A cardiac tamponade is a life threatening complication of transseptal punctures which occurs when a perforation is created at the left atrial wall, left atrial roof, or left atrial appendage. This perforation of the atrial wall leads to an accumulation of fluid within the pericardial cavity around your heart. This buildup of fluid compresses your heart which in turn reduces the amount of blood able to enter your heart. An inadvertent aortic puncture is a rare life threatening complication where the puncturing device enters and punctures the aorta which may require surgical repair. Moreover, for some puncture devices, it is difficult to ascertain the relative positioning between the puncture device and the supporting member. In some cases, visualization or mapping techniques may be used to ascertain such positioning. However, visualization or mapping may not always be readily available or desired.

In light of these potential complications associated with inadvertent puncturing and the difficulties associated with determining relative positioning between puncture device and supporting member, there exists a need to provide a novel radiofrequency puncturing method and devices wherein visual or tactile markers on the proximal end of the puncture device are used to assess the relative positioning between the puncture device (such as a radiofrequency puncture device) and a reinforcing member (such as a sheath or dilator). In an embodiment, the visual or tactile markers may be used for macro positioning while radiopaque markers at a distal end provide an ability to confirm or fine tune the positioning through visualization or mapping techniques.

In one broad aspect, the present inventors have discovered systems and methods that provide an RF wire and devices for supporting the same, in order to facilitate a transseptal puncture, for example using the inferior approach.

Inventors of the present invention have developed various embodiments of a novel system and method that involves providing, in one broad aspect, a puncture device having two components: (1) a puncturing component or member comprising markers at a proximal end and (2) a substantially rigid and or stiff supporting member that is removable or independent from the puncturing component or member, allowing the supporting member to be used selectively with the puncturing device. In an embodiment, the puncturing component or member comprises a substantially flexible tissue puncturing component or member. The substantially flexible tissue puncturing component or member may be substantially atraumatic. Additionally, the substantially flexible tissue puncturing component or member may have radiopaque markers at a distal end, visual or tactile markers at a proximal end, or both. In an embodiment, the substantially flexible tissue puncturing component or member is a radiofrequency (RF) wire.

Thus, in some embodiments, the puncturing component or member may be separated from the substantially rigid and/or stiff supporting member. The two components are independently operable and forms an assembly to thereby provide two separate and independent functionalities, (i) that of puncturing tissue with a substantially flexible and/or atraumatic component (such as a flexible energy delivery device but not limited thereto) and (ii) that of supporting the substantially atraumatic puncturing component using a substantially stiff or rigid component. Additionally, visual or tactile markers may be provided to determine the relative positioning between the puncturing component and the supporting member. These markers may be used alone or in conjunction with radiopaque markers provided at a distal tip of the puncturing component.

The advantages of the embodiments described herein may include one or more of:
- enabling the relative positioning between the substantially flexible puncture device and the substantially rigid supporting member to be visually or tactilely discernable by a user by using the markers at a proximal end of the substantially flexible puncture device;
- enabling both macro adjustment and micro adjustment of the positioning between the substantially flexible puncture device and the substantially rigid supporting member using a combination of visual/tactile markers and visualization/mapping techniques;
- enabling the substantially flexible puncture device to be usable separately from the substantially rigid supporting member to enable the substantially flexible puncture device to function as an exchange wire;
- enabling the substantially flexible puncture device to be usable in co-operation with the substantially rigid supporting member to allow sufficient force transmission and/or torque to be transmitted to the distal tip of the assembly (for example, to facilitate the drop down procedure to locate the fossa as described herein below) and to provide adequate support to facilitate puncture (using the substantially flexible puncture device and to facilitate crossing with the substantially flexible puncture device);
- enabling use of the substantially flexible puncture device to be usable separately from the substantially rigid supporting member as a guidewire;
- enabling the substantially flexible puncture device to be usable separately from the substantially rigid supporting member to minimize risk of damage to tissue, for example on the left side of the heart, by providing an atraumatic tip and reducing the amount of force needed to puncture tissue, for example, by using delivery of energy instead of mechanical force;
- enabling the substantially rigid supporting member to be removed or retracted to enable repositioning of the assembly against the target tissue site thus allowing the substantially rigid supporting member to be re-advanced over the substantially flexible energy delivery device for example, to repeat a drop down procedure in a transseptal puncture for positioning the assembly against the fossa;
- enabling the substantially rigid supporting member such as the needle shaft to be removed after puncturing, allowing the substantially flexible and atraumatic energy delivery device to be usable as an anchor after puncture by allowing it to remain positioned on the left side of the heart to maintain access to the left side of heart, and to additionally allow for track-ability of additional devices over the puncture device for guidance into the left side of the heart.

In an embodiment, provided is an assembly for a transseptal puncture procedure and enhancing procedural efficiency by facilitating exchange and positioning. The assembly comprises a puncture device for puncturing tissue and a supporting member for supporting member the puncture device. The puncture device comprises at least one proximal marker positioned at a proximal end of the puncture device, and at least one distal end marker which is visible under an imaging system. The supporting member comprises a lumen for receiving the puncture device and a distal tip marker which is visible under the imaging system. The puncture device is capable of being insertable within the lumen of the supporting member and being selectively usable in co-operation therewith during a portion of a procedure for puncturing tissue. Additionally: the puncture device is usable independently from the supporting member during another portion of the procedure. When the puncture device is inserted within the lumen, the at least one proximal marker allows the puncture device to be positioned relative to a proximal end of the supporting member. At the same time, the at least one distal tip marker of the puncture device and the at least one distal end marker of the supporting member allows the puncture device to be positioned relative to the supporting member by using the imaging system.

In an embodiment, the imaging system is a fluoroscopy system and the distal tip marker and distal end marker are visible under fluoroscopy.

In a further embodiment, the puncture device comprises an electrically conductive mandrel, wherein the at least one proximal marker is covering a proximal portion of the mandrel. In some such embodiments, a clear or translucent layer of insulation covers the mandrel and the at least one proximal marker, but does not cover the distal end of the mandrel such that the distal end of the mandrel is electrically exposed to define a distal tip electrode. In some such embodiments, the portions of the elongate puncture device at and adjacent the at least one proximal marker have a constant diameter.

In yet a further embodiment, the mandrel is surrounded by an oxide coating which is covered by the clear layer of insulation, wherein the at least one proximal marker comprises a portion of the mandrel not covered by the oxide coating such that said portion defines a visible marker. In some such embodiments, the visible marker is formed by mechanical grinding of the oxide coating. In some such embodiments, the oxide coating is comprised of titanium oxide.

In another embodiment, the mandrel is surrounded by a PTFE coating, and the at least one proximal marker comprises at least one pad printed marker on the PTFE coating defining a visible marker, wherein the PTFE coating and at least one pad printed marker are underneath the clear or translucent layer of insulation.

In yet another embodiment, the at least one proximal marker comprises a pad printed marker on the mandrel defining a visible marker. In some such embodiments, the pad printed marker is underneath the clear or translucent layer of insulation.

The clear or translucent layer may comprise a heat-shrink layer. In some such embodiments, the layer is comprised of polytetrafluoroethylene.

The mandrel may be comprised of nitinol, stainless steel, or a composite construction of a distal portion comprised of nitinol and a proximal portion comprised of stainless steel.

In some embodiments, the puncture device may comprise one or more of the following:
- an atraumatic distal tip
- a radiopaque coil which extends around a curve of the distal end portion which has a J-profile
- an end of the radiopaque coil can be used as the distal tip marker
- a radiopaque coil having echogenic properties when using ultrasound to enable visualization of the guidewire tip In an embodiment, the at least one proximal marker is an elongate marker comprising a leading edge and a trailing edge. In some such embodiments, when the leading edge is aligned with a predetermined distance from the proximal end of the supporting member, the distal tip of the puncture device is within the lumen of the supporting member. When the trailing edge of the proximal marker is aligned with the predetermined distance from the proximal end of the supporting member, the distal tip of the puncture device is exposed from a distal end of the supporting member. In some such embodiments, the elongate marker further comprises a midpoint, wherein when the midpoint is aligned with the predetermined distance from the proximal end of the supporting member, the distal tip of the puncture device is substantially aligned with the distal tip of the supporting member. In some such embodiments, the predetermined distance is between about 0 cm and to about 5 cm. In other such embodiments, the predetermined distance is between about 0 cm to about 1 cm. In some embodiments, the elongate marker comprises a midpoint marker to identify the midpoint.

In some embodiments, the puncture device is an energy based puncture device. In some such embodiments, the puncture device is a radiofrequency wire.

In yet another embodiment, a method of confirming a position of a tip of a transseptal puncture device relative to a supporting member is provided. The transseptal puncture device has at least one proximal marker which is visible to a naked eye and a distal tip marker which is visible under an imaging system and the supporting member has a distal end marker which is visible under the imaging system. In this embodiment, the following steps are provided:
  (i) positioning the elongate transseptal puncture device relative to a proximal end of the supporting member using the proximal marker without an imaging system in a macro-positioning step;
  (ii) turning on the imaging system; and
  (iii) positioning a distal tip of the elongate transseptal puncture device relative to an end of introducer by viewing the distal tip marker and distal end marker using the imaging system in a micro-positioning step.

In some such embodiments, the imaging system is a fluoroscopy system and the distal tip marker and distal end marker are visible under fluoroscopy.

In some embodiments, a method for puncturing a target tissue with a puncture device comprising at least one proximal marker is provided. In this embodiment, the following steps are provided:
  accessing a region of tissue within a patient's body by advancing the puncture device into the region of tissue;
  (ii) advancing a supporting device over the puncture device to support the puncture device, the supporting device comprising a lumen for receiving the puncture device;
  (iii) positioning the puncture device relative to a proximal end of the supporting member using the proximal marker without an imaging system in a macro-positioning step;
  (iv) positioning a distal end of the puncture device and a distal end of the supporting member at the target tissue site;
  (v) puncturing through the target tissue site using the puncture device, wherein the supporting member supports the puncture device through the puncturing.

In some embodiments, step (iii) further comprises using the proximal marker to determine that the distal tip of the puncture device is exposed from the distal end of the supporting device. In other embodiments, step (iii) further comprises using the proximal marker to determine that the distal tip of the puncture device is within the lumen of the supporting device.

In some embodiments, the method for puncturing tissue is a method for carrying out a transseptal procedure. The puncture device is a transseptal puncture device, and the target tissue is the fossa ovalis of a heart. In this embodiment:
  step (i) comprises advancing the transseptal puncture device into a superior vena cava;
  step (iv) comprises dropping the transseptal puncture device and supporting device from the superior vena cava into a heart of the patient to locate a fossa along a septum of the heart to position the device at the fossa
  the puncturing step (v) comprises puncturing the fossa to gain access to the left side of the heart.

In some embodiments, the method for puncturing tissue involves the additional step of positioning the puncture device relative to the supporting member using the proximal marker such that the distal tip of the puncture device is exposed from the distal end of the supporting member. In some such embodiments, the method may also include turning on an imaging system and positioning a distal tip of the elongate transseptal puncture device relative to an end of introducer by viewing the distal tip marker and distal end marker using the imaging system in a micro-positioning step. In this way, the proximal marker may be used in a macro-positioning step, and the imaging system may be used in a micro-positioning step.

In some such methods as described above, the puncture device is an energy based puncture device. The energy based puncture device may be a radiofrequency wire.

In some embodiments of the methods described above, the assembly used to carry out the method may further include a stylet. The stylet and the puncture device may be coupled together to provide a needle assembly, the assembly to be used as a more rigid puncture device.

In another embodiment of a method for puncturing tissue, the method comprises:
  advancing a flexible puncture device comprising a proximal marker into a region of tissue;
  advancing a sheath and a supporting member over the flexible puncture device into the region of tissue;
  withdrawing the flexible puncture device into the supporting member by using the proximal marker to determine the relative position between the flexible puncture device and the supporting member;
  positioning the flexible puncture device, the sheath and the supporting member as an assembly at a target tissue site in the region of tissue;
  Applying pressure on the target tissue site to tent using the supporting member;

advancing the flexible puncture device to a puncture position using the proximal marker to determine the relative position between the flexible puncture device and the supporting member;

creating a puncture in the target tissue site and advancing the flexible puncture device through the puncture; and advancing the sheath and supporting member over the flexible puncture device to cross through the puncture.

In another embodiment of a method for carrying out a transseptal procedure, the method comprises:

advancing an RF guidewire comprising a proximal marker into a superior vena cava;

advancing a sheath and dilator over the RF guidewire into the superior vena cava to form an assembly;

withdrawing the RF guidewire into the dilator by using the proximal marker to determine the relative position between the flexible puncture device and the supporting member;

dropping the assembly down from the superior vena cava into a heart to locate a fossa on a septum of the heart;

tenting the fossa using the dilator;

advancing the RF guidewire to puncture position for puncturing the fossa by using the proximal marker to determine the relative position between the flexible puncture device and the supporting member;

puncturing the fossa using energy delivered by the RF guidewire;

advancing the RF guidewire through the puncture; and advancing the sheath and dilator over the RF guidewire to cross the sheath and dilator through the puncture.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Some embodiments of the system provides a two part assembly comprising a flexible RF component and a rigid supporting member to enhance the utility of the system. The rigid member such as a reinforcing member is provided separate and removable from the flexible RF component (such as an RF wire) and as such can be introduced independently from the flexible RF wire. This provides flexibility in the manner in which the combination of the two components, the RF wire and the reinforcing member can be used. Initial advancement of the flexible RF wire in the absence of the reinforcing member removes the need for a separate exchange wire or guide wire to be used for initial access into the (superior vena cava) SVC. The reinforcing member can be advanced into the SVC to provide stiffness to the assembly to facilitate the drop down procedure to locate the fossa. If the initial pass at locating the fossa is unsuccessful the two part assembly enables partial removal or withdrawal of the rigid supporting member to enable the RF wire to be repositioned. The rigid supporting member may then be re-advanced to provide the adequate stiffness and force transmission to repeat the drop down procedure to locate the fossa and to provide adequate support to facilitate puncture and crossing of the tissue using the RF wire. As such, the rigid supporting member facilitates the transseptal puncture using the RF wire, and functions to additionally facilitate crossing into the left side after the puncture is completed. The reinforcing member may be removed thereafter leaving the flexible RF within the left side of the heart. The flexible RF wire is usable independently from the reinforcing member to facilitate anchoring in the left atrium of the heart, and to facilitate tracking of additional devices. This reduces the number of exchanges needed (i.e., there is no need to use a separate exchange or guide wire to anchor or track other devices), and minimizes risk of embolisms and/or trauma. Thus, the reinforcing member can be introduced selectively for a portion of the procedure that requires stiffness and can be removed thereafter (either partially or completely) in order to facilitate the remainder of the procedure. Furthermore, since the reinforcing component is provided separately from the flexible RF wire, the reinforcing component may be re-advanced or reinserted, as desired to complete aspects of the procedure.

In accordance with some embodiments of the present invention, details of the RF wire are disclosed in application number PCT/IB2013/060287 and publication number WO2015019132, which is incorporated herein by reference in its entirety. In addition and in accordance with some embodiments of the present invention, details of the supporting member usable with a puncture device such as the RF guidewire are disclosed in application number PCT/ib2017/056777 and publication number WO2018083599, which is incorporated herein by reference in its entirety.

In some embodiments of the present invention, an assembly is provided for puncturing tissue, where the assembly comprises a substantially flexible puncturing device (that is substantially atraumatic such as an energy based puncturing device) for puncturing tissue via delivery of energy. The assembly additionally comprises a supporting member for supporting the substantially flexible puncturing device such as a rigid needle shaft. In some such examples, the supporting member comprises a reinforcing member (which may form the needle shaft). The supporting member is operable to be selectively usable with the substantially flexible puncturing device and is detachable or removable therefrom. Additionally, the substantially flexible puncturing device is operable independently from the supporting member to puncture tissue. In some such examples, the substantially flexible puncturing device is an energy based device for delivering energy to puncture tissue.

The assembly enables the substantially flexible energy based puncturing device to be usable independently from the supporting member during a portion of the procedure and to be usable in co-operation with during a portion of the procedure. This reduces the number of exchanges needed by allowing the flexible energy based puncture device to be used for puncturing tissue and as an exchange wire. The puncturing device advantageously comprises an atraumatic tip for puncturing tissue as it utilizes energy to puncture tissue. The decoupling of the energy delivery portion of the assembly from the supporting member, additionally enables the supporting member to be removed if the flexible energy based puncturing device is not positioned at the desired target location, enabling the substantially flexible energy based puncturing device to be repositioned to enable the supporting member to be re-advanced over the substantially flexible energy based puncturing device to facilitate positioning of the energy delivery portion of the flexible puncturing device against the desired target tissue location and may additionally reducing procedure complexity and enhance procedural efficiency.

Example 1

Assembly Comprising Puncture Device and Supporting Member

Figure 1B:
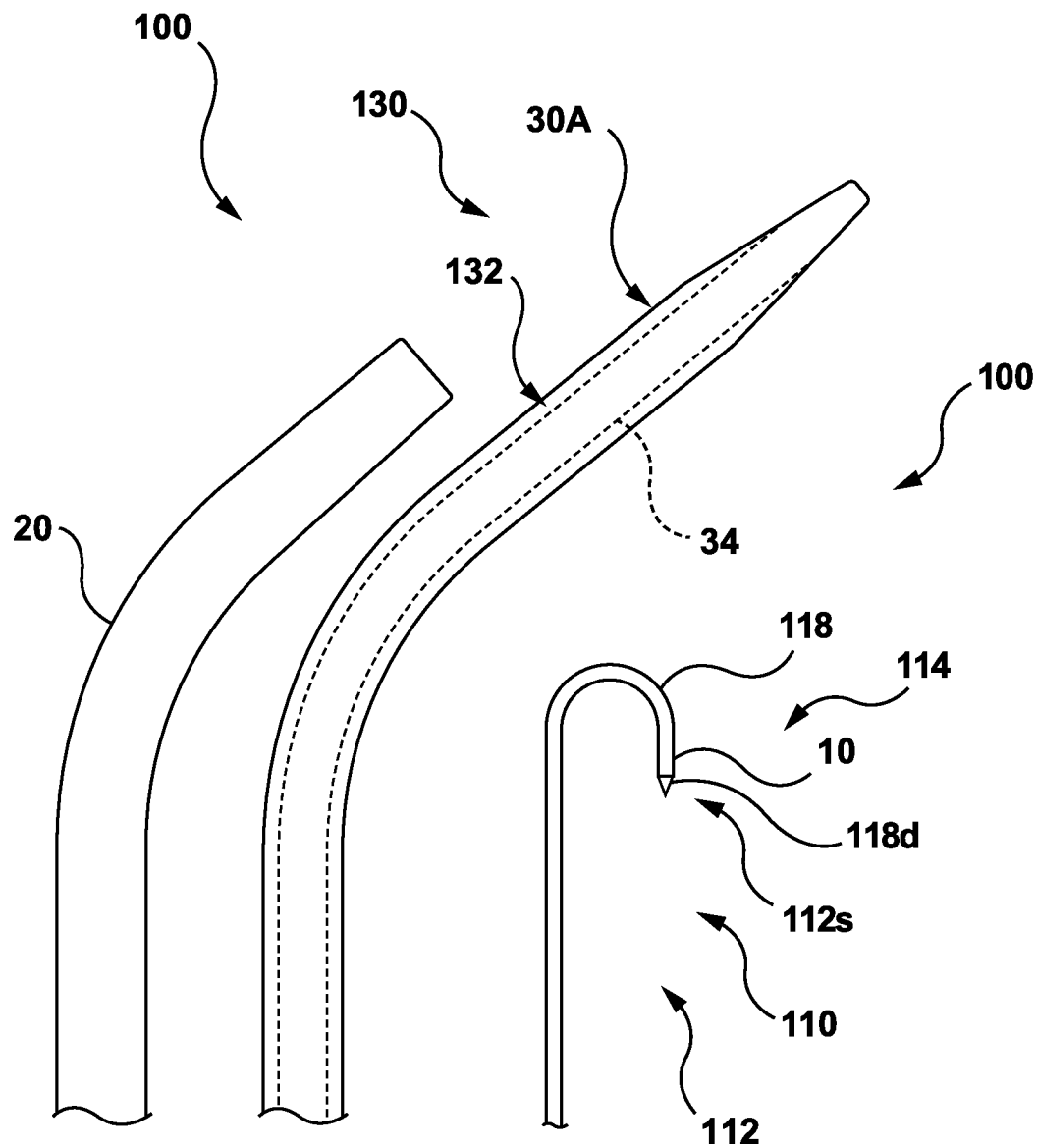

In some embodiments, as shown in FIGS. 1A and 1B, the present invention provides an assembly 100 for puncturing tissue such as for creating a transseptal puncture through a septum of a heart, where the assembly provides a tissue puncture or puncturing device 110, and a separate supporting member 130 that is selectively usable with the tissue puncture device 110 for supporting the puncture device 110. The puncture device 110 is capable of being selectively usable in co-operation with the supporting member 130 during one or more portions or steps of the procedure and the puncture device 110 is usable independently therefrom during another one or more portions or steps of the procedure, in order to puncture tissue. In some such embodiments, providing a separate puncture device 110 and a supporting member 130 for selective therewith additionally enhances procedural efficiency by facilitating exchange and positioning.

With respect again to FIGS. 1A and 1B, in some embodiments, an assembly 100 for puncturing tissue is provided, the assembly 100 comprising a substantially flexible puncture device 112 as discussed further herein below, for puncturing tissue and a supporting member 130 for supporting the substantially flexible puncturing device. The substantially flexible puncture device 112, similar to the embodiment discussed herein above, is capable of being selectively insertable within the supporting member 130 to be selectively usable in co-operation therewith during a portion of the procedure and wherein the substantially flexible puncture device 112 is usable independently therefrom during another portion of the procedure, in order to puncture tissue and to facilitate exchange and positioning. In some such examples, the substantially flexible puncture device 112 comprises an energy delivery device that is operable to deliver energy in order to puncture tissue. In some such examples, as described further in detail herein below, the supporting member 130 comprises a reinforcing member 34.

In one such example, the assembly 100 comprises a needle assembly for puncturing tissue, where the needle assembly comprises the puncture device 110 and the supporting member 130. In some such embodiments of a needle assembly, the puncture device comprises a substantially flexible puncture device 112, as shown in FIGS. 1A and 1B.

In a specific example of the needle assembly, as shown shown in FIG. 1A, the puncture device 110 comprises a substantially atraumatic distal tip 112d, wherein the puncture device 110 is substantially atraumatic. With reference again to FIG. 1A, in some embodiments, the puncture device 110 comprises an energy based puncture device 114 such as a substantially flexible energy based puncture device 114 that has an energy delivery portion or component 114d at the distal tip thereof for delivering energy in order to puncture tissue. In a specific instance of this example, the puncture device 110 comprises a flexible (radiofrequency) RF guidewire 10 that has a distal electrode tip 10d for delivering radiofrequency energy in order to puncture tissue.

In some instances, the RF guidewire 10 is a flexible wire which is generally electrically insulated save for selected distal regions such as the distal electrode tip 10d.

In a specific example of the needle assembly, as shown shown in FIG. 1A, the puncture device comprises a mechanical puncture device 118. In some such embodiments, of the needle assembly the mechanical puncture device 118 comprises a relatively sharp distal tip 118d for puncturing tissue.

In some such embodiments of the assembly 100 such as a needle assembly, as shown in FIGS. 1A and 1B, the supporting member comprises a reinforcing member. In some such embodiments, as shown, the supporting member 130 comprises a needle shaft 132 comprising the reinforcing member 34 for supporting the puncture device 110. In some such embodiments, the needle shaft 132 may provide or has properties of a mechanical needle, in a specific example, the reinforcing member [such as a metal hypo-tube] with one or more polymer layers is structured to form a needle shaft 132.
Supporting Member Comprising is Needle Shaft/Reinforced Dilator in one broad aspect, embodiments of the present invention provide an assembly IOU for puncturing tissue, the assembly 100 comprises a substantially flexible energy based (or energy delivery) puncture device 114 for puncturing tissue via delivery of energy and a supporting member 130 for supporting the substantially flexible energy delivery puncture device 114. The substantially flexible energy delivery puncture device 114 is capable of being selectively insertable within the supporting member 130 to be selectively usable m co-operation therewith during a portion of the procedure and wherein the substantially flexible energy delivery puncture device 114 is usable independently therefrom during another portion of the procedure, in order to facilitate exchange and positioning while providing substantially atraumatic puncture of tissue. In an example the supporting, member 130 comprises a reinforcing member 34.

In one such example, with reference now to the embodiment illustrated in FIG. 1A, the assembly 100 comprises a substantially flexible energy delivery puncture device or component 114 that is provided separately from and is operable independently from a supporting member 130. In one such example, the flexible energy delivery puncture device or component 114 (also referred to as a flexible energy based delivery device or a flexible energy delivery puncturing device) comprises a radiofrequency (RF) guidewire 10, and the separate supporting member 130 comprises needle shaft 132 comprising a reinforcing member 34 and one or more polymer layers 38 forming a polymer shaft 39 of the dilator 30A, where the reinforcing member 34 is substantially surrounded by the one or more polymer layers.
Puncture Device Comprising Modified Electrode Tip In the example shown, the RF guidewire 10 comprises an electrode for delivering radiofrequency energy. In one specific: example, as shown, the RF guidewire 10 has a distal electrode tip 10d for delivering, radiofrequency energy in order to puncture tissue. In some such embodiments, the distal electrode tip 10d is substantially atraumatic 10 reduce the pressure exerted on the tissue. In one such example, the distal electrode tip of the RF guidewire 10 comprises a substantially dome-shaped electrode tip that is substantially atraumatic to reduce the pressure exerted on the tissue.

In some such examples, with reference to FIG. 1A, the RF guidewire 10 may comprise a cylinder as shown by reference number 10c with a hemispherical electrode tip 10d which in some examples may form a cap that is formed distal to and adjacent to the cylinder 10c. In other words, the electrode tip 10d may be defined by a dome on top of the cylinder 10c, such as a substantially full round dome. In some such examples, the outer diameter of the dome may substantially match the outer diameter of the cylinder 10c. This may help provide a substantially atraumatic distal interface with the tissue to minimize risk of trauma and/or injury at the desired target tissue site. In some such embodiments, the dome shaped distal electrode tip 10d of the RF guidewire 10 may reduce the amount of pressure that is exerted by the distal tip on the issue to make the tip more atraumatic, so a force exerted by the distal tip is spread over a larger area. In some such examples, the RF guidewire 10 is provided as a 0.035" wire.

Figure 1C:
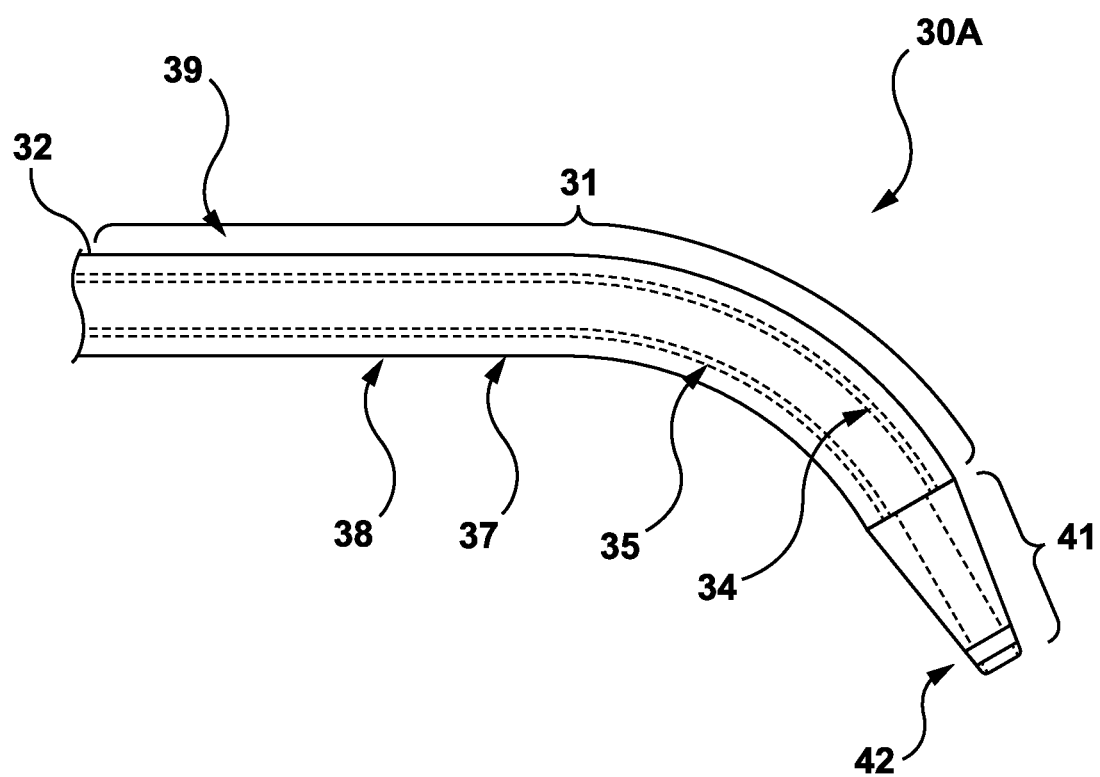
FIGS. 1C and 1D show a dilator comprising a reinforcing member in accordance with embodiments of the present invention.

More specifically, with reference to FIGS. 1A and 1C, the assembly additionally comprises a sheath 10 and a supporting member comprising a reinforced dilator such as dilator 30A that are usable with the flexible RF wire, where the dilator 30A comprises the reinforcing member 34 and one or more polymer layers 38 defining a polymer shaft 39 of dilator 30A, where the reinforcing member 34 is substantially surrounded by the one or more polymer layers 38.

In some such embodiments of the present invention, an assembly 100 is provided for puncturing tissue, where the supporting member 130 comprises a needle shaft 132 where the needle shaft 132 comprises the reinforcing member 34 and one or more polymer layers 38, where the reinforcing member 34 is substantially surrounded by the one or more polymer layers 38. In some such embodiments, the needle shaft 132 is provided within the dilator 30A. As such, in some embodiments, the supporting member comprises a needle shaft 132 that is provided as a part of or defined by the dilator 30A, wherein the needle shaft 132 is embedded in or surrounded by one or more polymer layers 38 of the dilator 130.

Details of the reinforcing member 34 are shown in FIG. 1C. More specifically, FIG. 1C illustrates a supporting member 130 that comprises a reinforced dilator 30A having the needle shaft 132, where the supporting member 130 is provided separately from the substantially flexible tissue puncturing device or member 112, such as an energy based tissue puncturing device 114 such as an RF guidewire 10. In one example, the needle shaft 132 is provided as a part of or in other words is defined by the dilator 30A. In some such examples, needle shaft 132 (and thus the dilator 30A defining the supporting member 130) is provided as a non-puncturing component for supporting the tissue puncturing device or member. In some such examples, the dilator 30A comprising the needle shaft 132 comprises a proximal portion 31 that terminates at a distal tip 41. In some such embodiments, the reinforcing member 34 provides sufficient rigidity that is substantially similar to that of a rigid needle.

In some such examples, a dilator shaft 32 extends along the proximal portion 31 and comprises the reinforcing member 34. In the particular example shown, the reinforcing member 34 is substantially surrounded by the one or more polymer layers 38. In some such examples the reinforcing member 34 is embedded within the one or more polymer layers 38 which comprise an inner polymer layer and an outer polymer layer. In some such examples, the inner and outer polymer layers comprise inner and outer tubular members 35, 37 of the dilator shaft 32. In some such examples, substantially surrounded may be taken to mean that the reinforcing member 34 is substantially surrounded on its outside or its exterior by the one or more polymer layers 38 that form a polymer shaft 39 (forming the dilator shaft 32) around the reinforcing member 34. In some embodiments, the dilator 30A may additionally include a radiopaque marker 42 at the distal tip 41. In one example, the reinforcing member 34 comprises a hypo-tube such as a metal hypotube. In one such example, the reinforcing member 34 comprises a stainless steel hypotube and the inner and outer tubular members 35, 37 comprise HDPE.

Supporting Member Comprises a Hypo-Tube which Defines an Inner Lumen

In one such example, the reinforcing member 34, such as the stainless steel hypo-tube, extends longitudinally within the one or more polymer layers, for example, within the inner and outer tubular members 35, 37, as shown in FIG. 1C. As such, the reinforcing member 34 (for example a hypotube) defines an inner lumen of the supporting member 130.

In one example, the supporting member 130, with reference again to FIG. 1C, the one or more polymer layers 38 comprise an inner polymer layer and an outer polymer layer, which in some examples may comprise inner and outer tubular members 35, 37. In a specific instance, the reinforcing member 34 is substantially surrounded by the one or more polymer layers 38 along its exterior, as noted above. In other examples, the reinforcing member 34 is substantially surrounded by the one or more polymer layers 38 such that the reinforcing member 34 is located between the inner polymer layer and an inner polymer layer, for example, as defined by the inner and outer tubular members 35, 37 shown in FIG. 1D (in some examples, the hypo-tube is located between or sandwiched between two layers of polymer. In other words, the reinforcing member 34 is substantially surrounded by and embedded within both the inner and outer polymer layers. In other words the reinforcing member 34 is sandwiched or located between the inner and outer polymer layers 38 and thus the polymer shaft 39 that forms the dilator shaft 32. In some such examples, the inner and outer tubular members 35, 37 comprise high density polyethylene (HDPE).

In some embodiments of the transseptal assembly 100, the sheath 10 comprises a standard transseptal sheath, the needle shaft 132 (provided as a part of or defined by the dilator 30A) comprising a reinforcing member 34 as described herein above and the RF guidewire or RF wire is provided as a 0.035" wire. In some such examples, the RF wire comprises a J-tip wire or in alternate examples the RF wire comprises a pigtail wire.

In some such embodiments of the present invention, the reinforcing member 34 comprises a distal end 34D and a proximal end 34P, where the reinforcing member 34 extends within an inner lumen of the dilator 30A, as shown in FIG. 1C. In some such embodiments, the assembly 100 provides a substantially gapless interface at the junction between the reinforcing member at the distal and proximal ends and the one or more polymer layers. In some such examples, the reinforcing member 34 is secured within the one or more polymer layers 38 forming the polymer shaft 39 of the dilator 30A. In one such example, the reinforcing member 34 is substantially affixed at its distal and proximal ends (in other words the reinforcing member distal and the reinforcing member proximal end) to the one or more polymer layers 38 of the dilator 30A to provide a substantially gapless interface at the junction between the reinforcing member 34 at the distal and proximal ends and the one or more polymer layers 38 reinforcing member. The drawings show the interface at the distal end of the reinforcing member 34. A similar interface is provided at a proximal end of the reinforcing member 34. In some such embodiments of the present invention, the reinforcing member 34 is substantially sealed at its distal and proximal ends (in other words at the reinforcing member distal end and the reinforcing member proximal end) to the one or more polymer layers 38 of the dilator 30A. In some such embodiments, by substantially eliminate the gap between the reinforcing member 34 and the polymer shaft 39 of the dilator 30A, this may prevent blood or other liquid from getting between the reinforcing member 34 and the polymer shaft 39.

Supporting Member Providing Force Transmission/Torque

The supporting member 130 provides stiffness to the puncturing device such as the RF wire to enable force transmission to enable force to be transmitted to a distal end of the assembly 100. The supporting member 130 provides sufficient stiffness to the puncturing device to enable torque to be transmitted to a distal end of the assembly.

Reinforcing Member Providing Force Transmission/Torque

In some such examples, the reinforcing member 34 provides sufficient stiffness to the supporting member 130 to enable sufficient force transmission to enable force to be transmitted to a distal end of the assembly 100. More specifically, the reinforcing member 34 provides sufficient stiffness to the assembly 100 such that the substantially flexible puncturing device 112 (such as a substantially flexible energy based puncture device 114 such as an RF wire 10) together with the supporting member 130 is capable of sufficient force transmission to enable force to be transmitted to a distal end of the assembly 100 (and thus allows force to be transmitted to a distal end of the substantially flexible puncturing device 112).

As such, the reinforcing member 34 is capable of imparting force transmission capabilities to the substantially flexible RF wire 10, which when used together with the supporting member 130 is capable of force transmission to enable force to be transmitted to a distal end of the assembly 100, for example for engaging tissue at a target tissue site. As such the reinforcing member 34 functions as a force transmitting portion of the assembly 100.

In some such examples, the assembly 100, further comprises a sheath 20, as shown in FIG. 1A, where the sheath 20 is usable with the supporting member 130, to provide stiffness to the assembly 100 to facilitate force to be transmitted to a distal end of the assembly 100.

In some such embodiments of the present invention, the reinforcing member 34 provides sufficient stiffness to enable torque to be transmitted to a distal end of the assembly 100. As such, the reinforcing member 34 provides sufficient stiffness to the assembly, wherein the substantially flexible puncturing device 112 such as a substantially flexible energy based puncturing device 114 together with supporting member 130 provides sufficient stiffness to the assembly 100 to enable torque to be transmitted to a distal end of the assembly 100 (and thus allows torque to be transmitted to a distal end of the substantially flexible puncturing device 112).

Some such embodiments of the present invention facilitate transseptal puncture, where the reinforcing member 34 provides sufficient stiffness to the assembly 100 to enable sufficient force transmission for engaging a desired tissue site (such as the septum of the heart). In some such example, the supporting member 130 provides the substantially flexible puncture device 112 with force transmission capabilities where the substantially flexible puncture device 112 is capable of force transmission when in use with the supporting member 130.

In some such embodiments, the assembly 100 further comprises a sheath 20, as shown in FIG. 1A, where the sheath 20 is usable with the supporting member 130, to provide stiffness to the assembly 100 to enable torque to be transmitted to a distal end of the assembly 100.

In some such examples, the sheath 20 may be coupled to the dilator 30A which enables force and/or torque transmission using one or more of the components [i.e., the sheath 20 or the dilator 30A.]. In other words, the user may not have to manipulate the sheath 20 and the dilator 30A (the user may just manipulate the sheath 20 or the dilator 30A) and the RF guidewire 10 follows the guidance and/or direction of the sheath 20 and/or the dilator 30A. In some such examples, the sheath 20 has some contribution to the overall torque. In some such embodiments, torqueing the sheath 20 and/or the dilator 30A enables the reinforcing member 34 to be torqued therewith.

Stiffness of the Reinforcing Member

In some embodiments of the present invention, the force transmitting portion of the assembly 100 has a force transmitting portion flexural rigidity of at least about 0.0085 $Nm^2$, for example about 0.0115 $Nm^2$. In some embodiments of the present invention, the force transmitting portion of the assembly is the supporting member 130 that has a stiffness or rigidity with a flexural rigidity value of at least about 0.0115 $Nm^2$ to enable sufficient force transmission to enable force to be transmitted to a distal end of the assembly 100. In some such examples, the supporting member has a flexural rigidity of about 0.0085 $Nm^2$ to about 0.0145 $Nm^2$. In one such example, the supporting member 130 is the reinforced dilator 30A that has a flexural rigidity of at least about 0.0085 $Nm^2$, for example about 0.0115 $Nm^2$. In a specific example, the reinforced dilator 30A has a flexural rigidity about 0.0085 $Nm^2$ to about 0.0145 $Nm^2$. In one such example, the reinforced dilator 30A is the reinforced dilator 30A as provided in Example 1, for example as provided with respect to FIGS. 2A-2G.

In some such examples, the supporting member 130 functions to impart rigidity or stiffness to the assembly 100 including the puncture device such as a substantially flexible puncture device, to provide force transmission capabilities to the assembly including the puncture device such as a substantially flexible puncture device.

In some examples, the flexural rigidity values provided for the supporting member 130 are also usable for Example 2 provided herein with respect to FIGS. 4A-4G.

In some embodiments of the present invention, the force transmitting portion of the assembly is the supporting member 130 that is the reinforcing member that comprises the stylet. The stylet has a stiffness or rigidity with a flexural rigidity value of at least about 0.008 $Nm^2$, for example about 0.015 $Nm^2$ to enable sufficient force transmission to enable force to be transmitted to a distal end of the assembly 100. In some such examples, the supporting member has a flexural rigidity of about 0.008 $Nm^2$ to about 0.024 $Nm^2$.

Stiffness of the Puncture Device

In some embodiments of the present invention, a distal portion of the puncture device such as a substantially flexible puncture device has a distal portion or distal region flexural rigidity. In some such examples, a substantially flexible RF guidewire 10 is provided, where the substantially flexible RF guidewire 10 has a distal portion [including along the distal electrode tip 10d] where the RF guidewire 10 has a distal portion stiffness defined by a flexural rigidity of at least about $3.57 \times 10^{-6}$ $Nm^2$, for example about $4.76 \times 10^{-6}$ $Nm^2$. In some embodiments of the present invention, RF guidewire 10 has a distal portion stiffness or rigidity with a flexural rigidity of between about $3.57 \times 10^{-6}$ $Nm^2$ to about $5.95 \times 10^{-6}$ $Nm^2$.

In some such examples, the distal region of the RF guidewire 10 is tapered down from a proximal region of the RF guidewire 10, over about 12 cm-15 cm. In other words, the distal portion of the RF guidewire 10 has a length of between about 12 cm to about 15 cm. In some such examples, the distal portion of the RF guidewire 10 is the thinnest point of the RF guidewire 10.

In some such embodiments, the substantially flexible RF guidewire 10 has a proximal portion with a proximal portion flexural rigidity of less than about 0.00179 $Nm^2$, for example about 0.00143 $Nm^2$. In some embodiments of the present invention, RF guidewire 10 has a proximal portion stiffness or rigidity with a flexural rigidity of between about 0.00107 $Nm^2$ to about 0.00179 $Nm^2$.

In some embodiments of the present invention, where the substantially flexible puncture device comprises an RF guidewire 10 has a flexural rigidity of between about $2.0 \times 10^{-6}$ to about $1.4 \times 10^{-3}$ $Nm^2$. In some such examples, the RF guidewire 10 has a wire diameter that is between about 0.127 mm to about 0.635 mm.

Supporting Member/Reinforcing Member Shape-Ability

The reinforcing member 34 is shapeable to enable the supporting member 130 (for example comprising a needle shaft 132 as provided as a part of or defined by a reinforced dilator 30A) to be removed from the substantially flexible energy delivery puncturing device 110 (such as the RF wire 10) to enable a curve of the supporting member 130 be re-shaped to be reinserted therewith, in order to optimize the position of the assembly 100 against a target tissue site, such as the fossa of the septum of the heart. In other examples, the supporting member 130 comprises a stylet 60 that is provided separately from the dilator 30A (as described in embodiments described further herein below and imparts shippability to the assembly 100. In other words the stylet 60 functions to impart a desired curvature and stiffness to the assembly 100 when in use with the assembly 100. The stylet 60 is removable from the assembly and can be re-shaped and re-inserted into the assembly 100 to provide a desired curvature to the assembly 100.

Coupling Between Dilator and Sheath (Locking Feature)

In some embodiments of the present invention, with reference now to FIG. 1C, and assembly 100 is provided that comprises a sheath 20 as shown in FIG. 1A for use a sheath for use with the reinforced dilator 30a for use therewith during a portion of the procedure. In some such examples, the assembly 100 comprises a locking mechanism to enable axial and rotational coupling of the dilator 30A with the sheath 20 for a portion of the procedure. In some embodiments of the present invention, the locking mechanism enables co-operative engagement between the sheath 20 and dilator 30A to provide rotational and axial coupling. This may help minimize the risk of rotational misalignment between the sheath 20 and dilator 30A and thus may reduce the risk of confusion resulting from the misalignment.

Figure 1D:
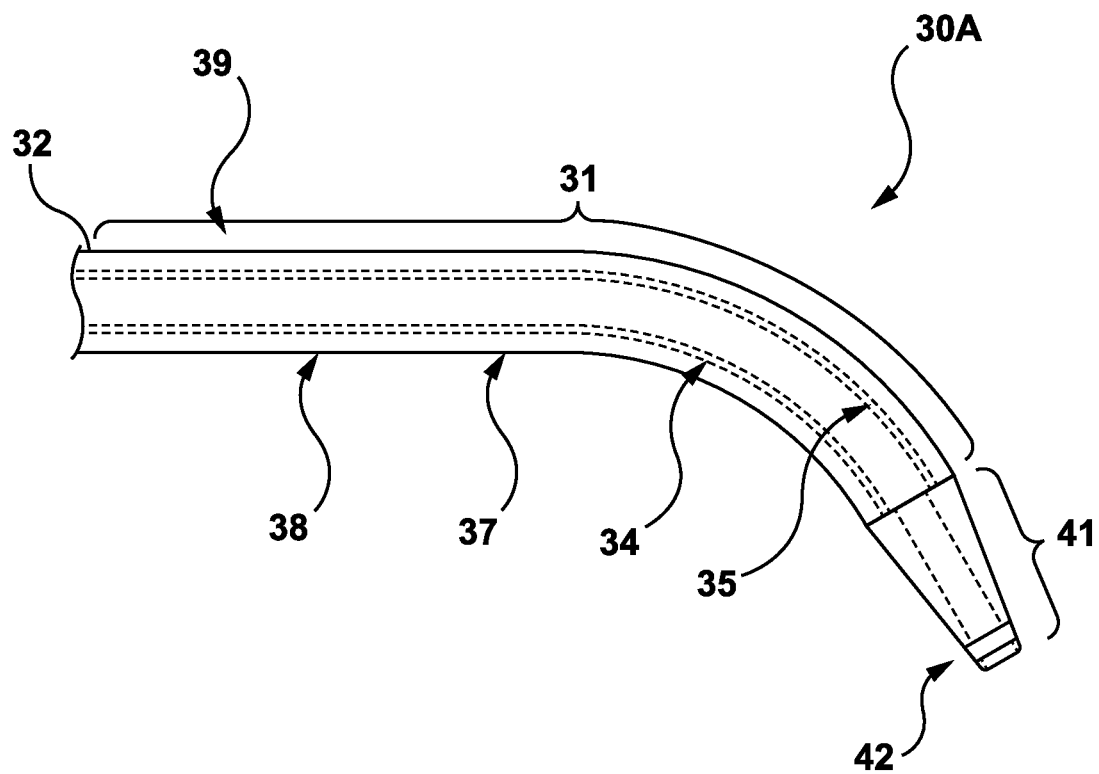
Figure 1E:
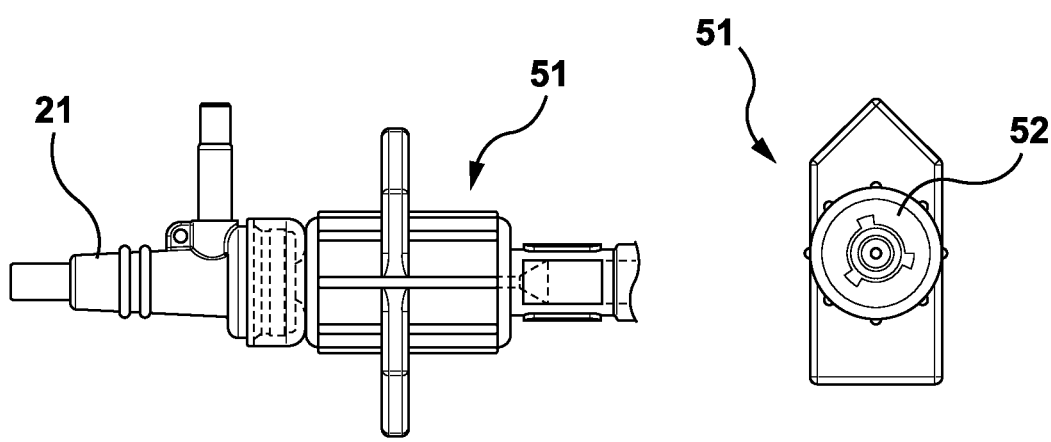
FIG. 1E shows a locking mechanism for enabling coupling of a sheath and dilator during use, in accordance with an embodiment of the present invention.
Figure 1F:
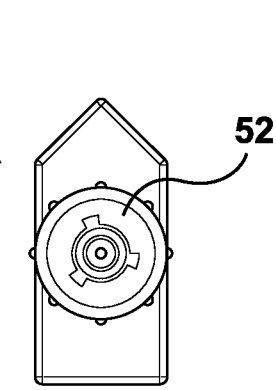
FIG. 1F is an illustration of a dilator hub with keys for enabling locking of the dilator hub to the sheath hub, in accordance with an embodiment of the present invention.

Referring now to FIG. 1E, the supporting member 130 comprising a needle shaft 132 (as provided as part of or defined by) dilator 30A comprises a dilator hub 51 that is operable to be coupled to the sheath hub 21 for a portion of the procedure. In one example, as illustrated in FIG. 1F, a locking mechanism is provided where the dilator hub 51 comprises one or more keys 52 for co-operatively engaging with corresponding features (such as key receiving features) on the sheath hub 21 that enable axial and rotational locking with the sheath 20. As such in some embodiments of the present invention a locking mechanism is provided to enable axial and rotational coupling of the dilator with the sheath for a portion of the procedure. In some examples, a steerable sheath is provided, where the steerable sheath 20 may be an 8 Fr steerable sheath. Alternatively, an 8.5 Fr steerable sheath 20 may be provided. In some such examples, the steerable sheath 20 may be provided with different curvatures. In a specific example, steerable sheaths 20 may be provided in different curvatures, specifically at angles of: 37, 45, 55, 90, or 135 degrees. In a specific instance of this example, the sheath tubing comprises an inner PTFE liner, a braid and a Pebax outer jacket. In some such embodiments, a supporting member 130 comprising a needle shaft 132 (for example, provided as a part of or defined by) an 8 Fr dilator 30A is provided that is compatible with an 8 Fr Sheath. Alternatively, supporting member 130 comprising the needle shaft 132 may be provided as a part of, or defined by an 8.5 Fr dilator 30A may be provided that is compatible with an 8 Fr steerable sheath 20. The supporting member 130 comprising the needle shaft 132 (for example as provided as a part of or defined by dilator 30A) may be provided with a 50 degree or 86 degree curvature. In some examples, materials may include HDPE and a metal hypotube that forms the reinforcing member 34. In some such examples, the RF wire comprises a 0.035" OD wire and may be a J-tip wire or a pigtail wire. In a specific instance of this example, the wire may comprise a stainless steel core with a PTFE coating.

Markers Along the Length of the Puncture Device

Markers may be placed at discrete locations along the length of a puncture device. Various embodiments are described below. Markers are particularly advantageous in embodiments where the puncture device does not have handle or hub. Some RF puncture devices, for example, do not have a handle or hub. This is similar to an exchange wire or guide wire. However, macro-positioning of the puncture device relative to the supporting member may be needed during certain procedures. Accordingly, visual or tactile markers may be provided to assist in determining such relative positioning. Visual markers are visible to a user without the use of an imaging system i.e. it is visible by the naked eye. Tactile markers may be both visible to a user and discernable by touch.

Figure 1G:
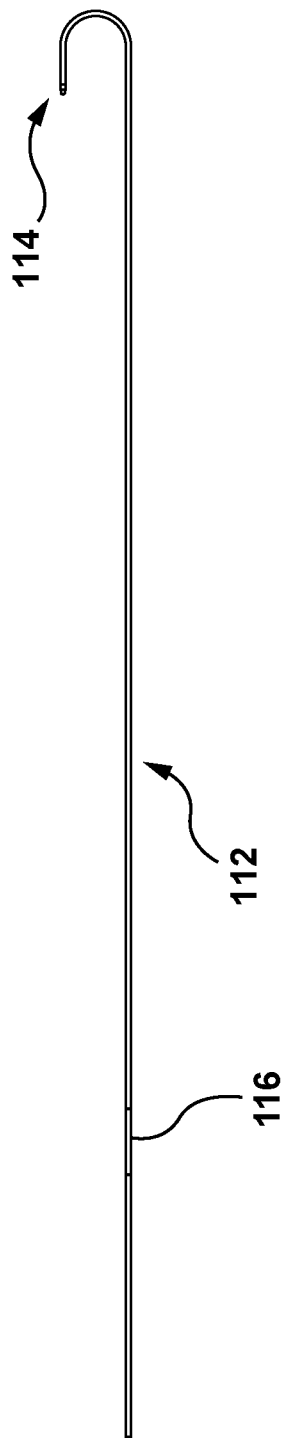
FIG. 1G is an illustration of a puncture member with a proximal marker, in accordance with an embodiment of the present invention.

In some embodiments, as shown in FIG. 1G, puncture member comprises a proximal marker 116. Laser etching can be used to form proximal marker 116 so that it cannot be removed during use or sterilization. The use of proximal marker 116 is described below.

Figure 1H:
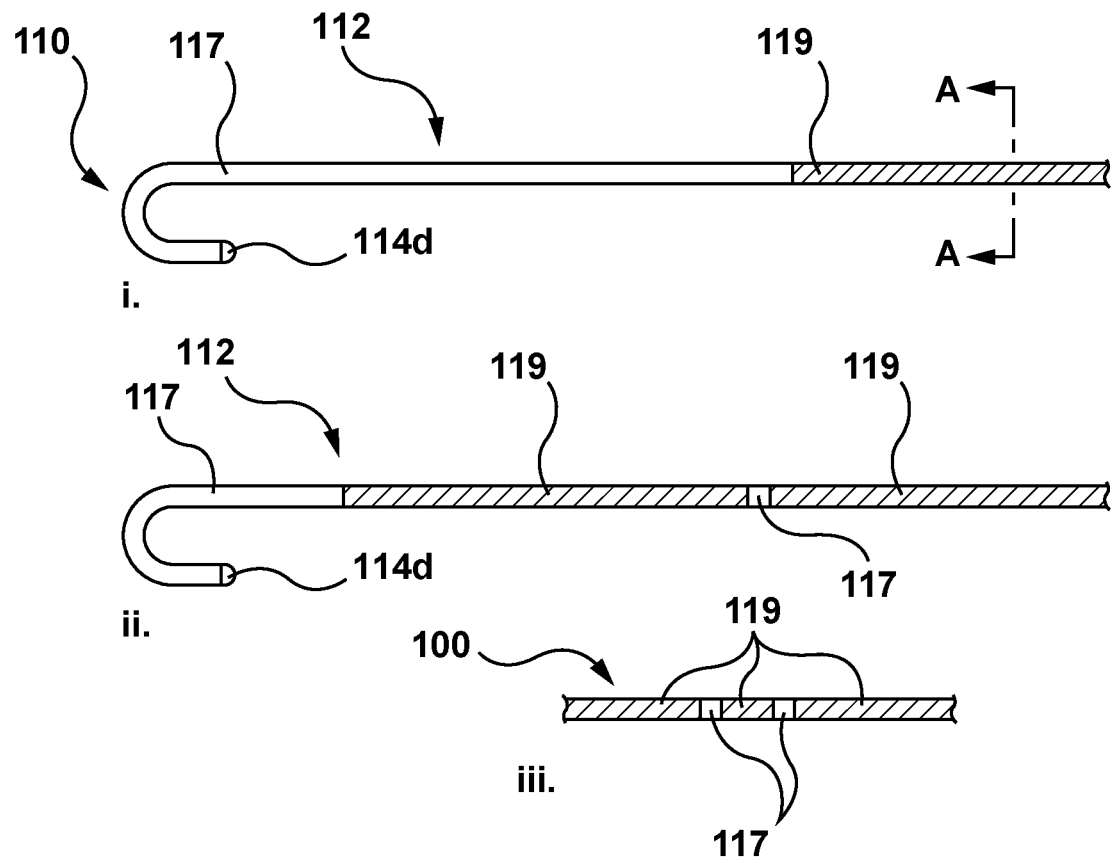
FIGS. 1H-1I is an illustration of a puncture member with a marker, in accordance with an embodiment of the present invention.
Figure 1I:
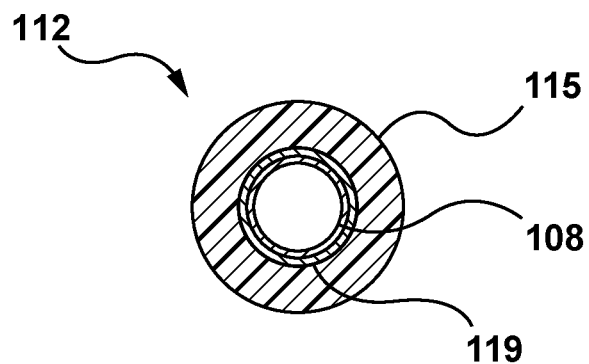

FIG. 1H shows different examples of marker 117. FIG. 1H-i shows a distal end marker 117. FIG. 1H-ii shows a distal end marker 117 and an intermediate marker 117. FIG. 1H-iii shows two intermediate markers 117. Proximal marker 116 of FIG. 1G or 5A-5C could be formed by removing an oxide as described below and covering the wire with a clear layer.

In an embodiment, markers may be constructed by making the markers a different color than the rest of the puncture device body. This may be achieved by a number of means. In one embodiment, the puncture device 112 is stainless steel. The puncture device 112 is masked at discrete locations along the body (i.e., where the markers will be) while the rest of the wire is coated with a first PTFE layer that is a different color than the underlying stainless steel surface. The PTFE coating may be applied using a sprayable PTFE. After coating process is complete, the masking is removed. An additional layer of clear PFTE may be applied, e.g., using a heat shrinking process to bond the layer to the puncture device. The previously masked portions then become markers which are visible to the naked eye. Depending on the thickness of the first PTFE layer, the marker may also become a "tactile" marker. In other words, a user may touch the markers and detect a narrower portion of the wire.

Other means of making markers include:
a. Applied a layer of PTFE coating with a first color. Markers may then be pad printed at discrete locations where markers are desired.
b. Applying a layer of PTFE coating with a color. Mechanically grinding away the PTFE coating at discrete locations where markers are desired. In this embodiment, another layer of clear PTFE coating may be applied (e.g., by heat shrinking).
c. Pad printing markers onto the puncture device body. Then, applying a layer of clear or translucent PTFE heatshrink over top. The layer of clear or translucent PTFE must be sufficiently translucent such that the underlying pad printed markers are visible.

In an alternative embodiment, puncture device 112 includes one or more markers 117 formed by mechanical grinding of an oxide coating of the wire created during heat treatment of the wire. Some embodiments of puncture device 112 include one or more marker 117 formed by mechanical grinding of an oxide coating of the wire created during heat treatment of the wire. Marker 117 can be a proximal marker, an intermediate marker, or a distal marker. The formation of said markers is described making reference to FIGS. 1H and 1I. FIG. 1I shows a cross-section of wire at point "A" of FIG. 1H after the wire is heat treated. FIG. 1I illustrates puncture device 112 comprising a solid mandrel surrounded by oxide coating 119 which is covered by clear heat-shrink 115 (a clear layer). In typical embodiments mandrel 108 is comprised of nitinol while in some alternative embodiments it is stainless steel. In one embodiment, the oxide coating 119 on the puncture device is comprised of titanium dioxide. This coating is typically stable and acts as a barrier against ion exchange. After the heat treatment, oxide coating 119 extends the full length of the puncture device. Typically a portion of the coating at the proximal end is removed to allow electrical connection with the over wire cable connectors and at least one other portion of the coating is removed to form a marker visible without imaging i.e. visible to an unaided eye. The oxide coating 119 can be removed by grinding the surface of the puncture device to the desired profile to thereby form a marker 117. Clear heat-shrink 115 typically comprises a clear PTFE formed from an extruded tube that that is heat shrunk onto the puncture device. Alternative embodiments of heat-shrink 115 are comprised of a clear layer formed from alternative materials known to those skilled in the art. The RF guidewire 100 is electrically insulated by the clear heat-shrink which allows a marker 117 to be visible. In some examples, the clear layer has a thickness ranging from about 0.086 mm to 0.118 mm.

Figure 5A:
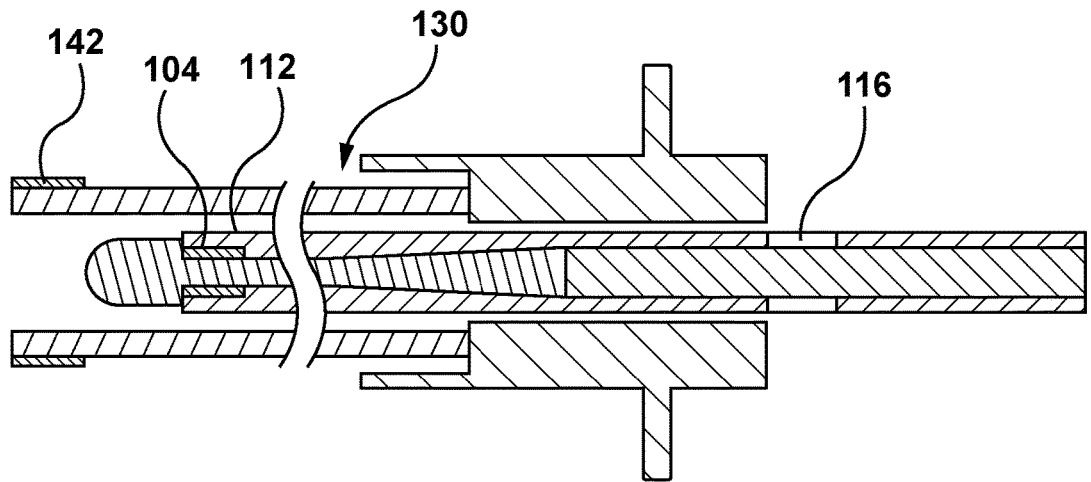
FIGS. 5A-5C are diagrammatic cross-sectional views of a supporting member with a puncture device installed therein.
Figure 5B:
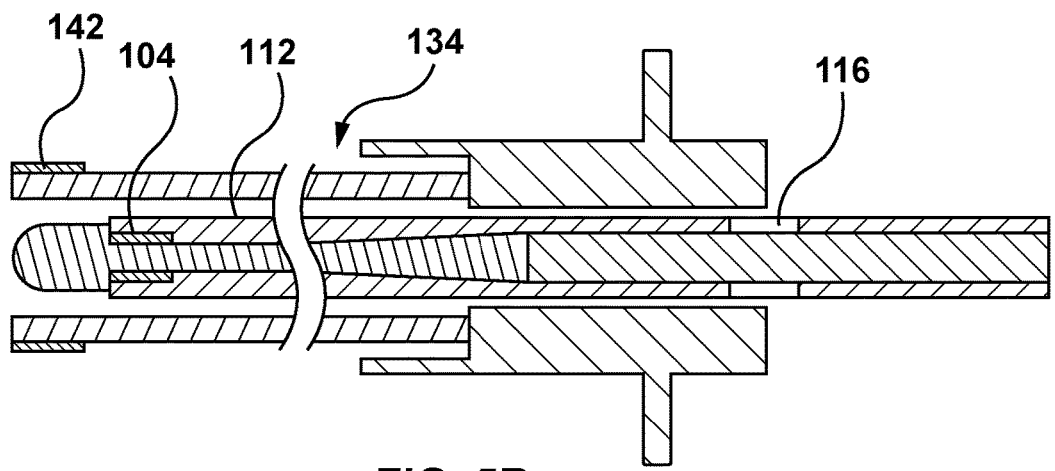
Figure 5C:
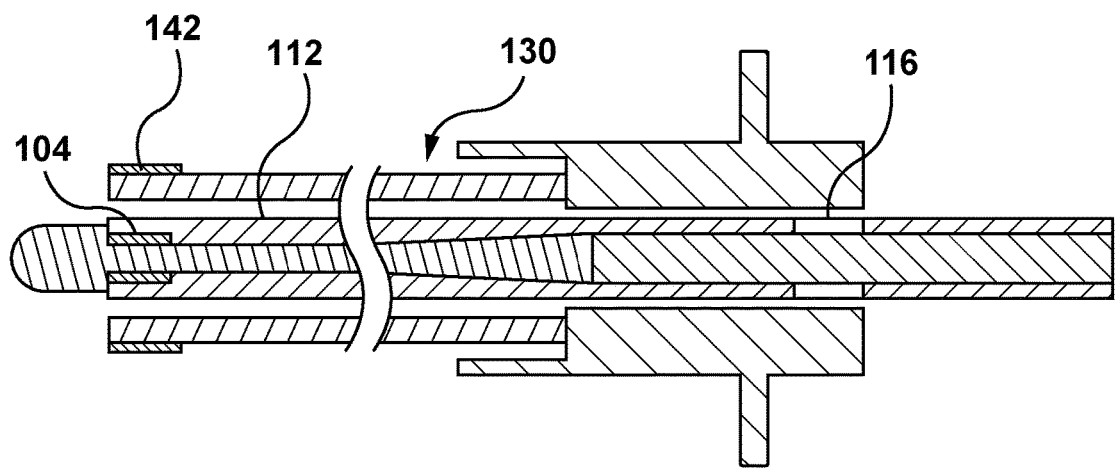

FIG. 5 is a diagrammatic cross-sectional view of a supporting member 130 with a puncture device 112 (such as an RF guidewire) installed therein. In the embodiment of FIG. 5, supporting member 130 has a distal marker 142 at its distal end for indicating the position of the distal end of supporting member 130 under imaging, and the puncture device 112 has a radiopaque marker 104 at its distal end for indicating the position of the distal end of the puncture device under imaging. FIGS. 5A to 5C show the steps of a method advancing puncture device 112 through the supporting member 130. In FIG. 5A shows the puncture device 112 is positioned to have the distal end of proximal marker 116 at the proximal end of the hub/handle of the supporting member while the tip of the tip of the puncture device still inside of the lumen of the supporting member. The puncture device is advanced to the configuration of FIG. 5B wherein the middle of proximal marker 116 at the proximal end of the hub/handle of the supporting member and the tip of the puncture device lines up with the tip of the supporting member 130. The puncture device is further advanced to the configuration of FIG. 5C wherein the proximal end of proximal marker 116 is at the proximal end of the hub/handle of the supporting member and the tip of the puncture device 112 extends beyond the tip of the supporting member 130. The configuration on FIG. 5C further includes distal marker 142 of supporting member 130 lining up with radiopaque marker 104 at of the distal end of supporting member 130, which under imaging, would confirm the relative positioning of the puncture device and the supporting member. Thus, FIGS. 5A-5C illustrates an elongate proximal marker 116 such that the leading edge of the marker represents a first relative position between puncture device and supporting member (i.e., where the puncture device is well within the lumen of the supporting member), the middle (or midpoint) of the marker represents a second relative position between puncture device and supporting member (i.e., where the distal tip of the puncture device is aligned with the distal tip of the supporting member), and the trailing edge of the marker represents a third relative position between puncture device and supporting member (i.e., where the distal tip of the puncture device is beyond the distal tip of the supporting member and exposed therefrom). In an alternative embodiment, the respective relative positions may be marked by separate markers. In an alternative embodiment, a plurality of separate proximal markers may be provided to respectively identify the first relative position, the second relative position, and the third relative position.

In some embodiments, the shaft of puncture device 112, radiopaque marker 104, and proximal marker 116 have outer diameters <=0.035". Radiopaque marker 104 is comprised of platinum and iridium (Pt/In and has an inner diameter >=0.01". In one embodiment, the mandrel of the puncture device 112 is made of stainless steel. In an alternative embodiment, the mandrel of the puncture device 112 is a composite of a distal portion comprised of a super elastic material such as Nitinol which is designed to be kink resistant, and a proximal portion comprised of a stiffer alloy such as stainless steel. In still another embodiment, the mandrel is comprised of Nitinol for greater flexibility and resistance to kinking along the entire length of the puncture device. In the embodiment where there is a composite construction, these materials can be welded, pressfit or glued together. The body of puncture device may be completely insulated with polytetrafluoroethylene (PTFE). While typical embodiments of puncture device 112 have an outer diameter of <=0.035", any size outer diameter of the puncture device is acceptable as long as it fits within the dilator used for a transseptal procedure. Alternative embodiments of radiopaque marker 104, which are components of smaller diameter RF guidewires, have an inner diameter smaller than 0.01". While a typical embodiment of introducer 130 has an inner diameter of >=0.035", other inner diameter sizes of the introducer are possible so long as the RF guidewire 100 used in a procedure can pass through.

In one embodiment, puncture device may comprise multiple markers along its length. These markers may be spaced such that they correspond with a particular length of supporting member. Supporting members, such as dilators, sheaths, and stylets may be of varying lengths. For example, a sheath may be longer or shorter depending on the needs of the particular procedure. By providing multiple markers spaced along the length of a puncture device, the puncture may be used with supporting members of a variety of lengths by matching a marker with a particular supporting member length. To make it more clear, markers may be provided with distinct visual or tactile features to distinguish which markers should be used with which devices. For visual markers, different colours, shades, surface features (reflective metallic coils, dimpled bands, knurls, etc.) or symbols may be used to distinguish between different markers. For markers with visual features, a clear coating is provided over top to secure the feature and ensure that the puncturing device has a consistent outer surface.

Radiopaque Markers

In some embodiments, as shown in FIGS. 1C and 1D, the supporting member 130 comprises one or more radiopaque markers such as a supporting member radiopaque marker 42. In some such examples as above, the assembly 100 provides a supporting member 130 (for example comprising a needle shaft 132 as provided as a part of or defined by a reinforced dilator 30A), comprises a radiopaque marker 42, such as at the distal tip of the supporting member 130. In some such examples, the supporting member 130 comprises a radiopaque marker 42 embedded within the polymer of the distal tip thereof, as shown.

In a specific example, the radiopaque marker 42 comprises a radiopaque coil embedded within the polymer of the supporting member 130 (for example comprising a needle shaft 132 as provided as a part of or defined by a reinforced dilator 30A) such as within the one or more polymer layers 38 (forming the polymer shaft 39 which in turn forms the dilator shaft 32), for example, at a distal tip thereof (of the supporting member 130). In a more specific example, the radiopaque coil is embedded within the one or more polymer layers such that the one or more polymer layers extend distally beyond the radiopaque coil.

Alignment Using Radiopaque Markers

Figure 3A:
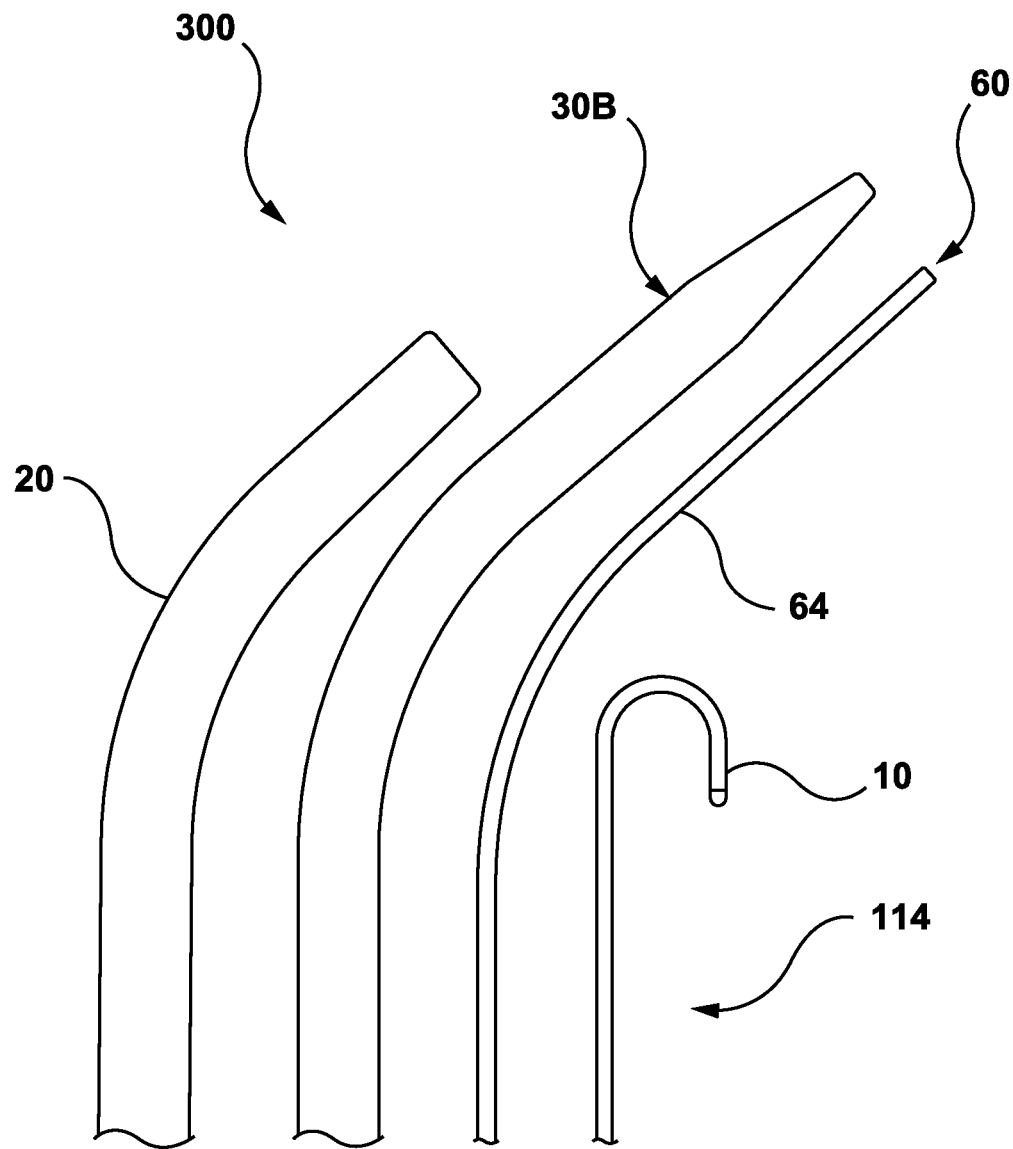
FIG. 3A is an illustration of a transseptal assembly in accordance with an alternate embodiment of the present invention.
Figure 3B:
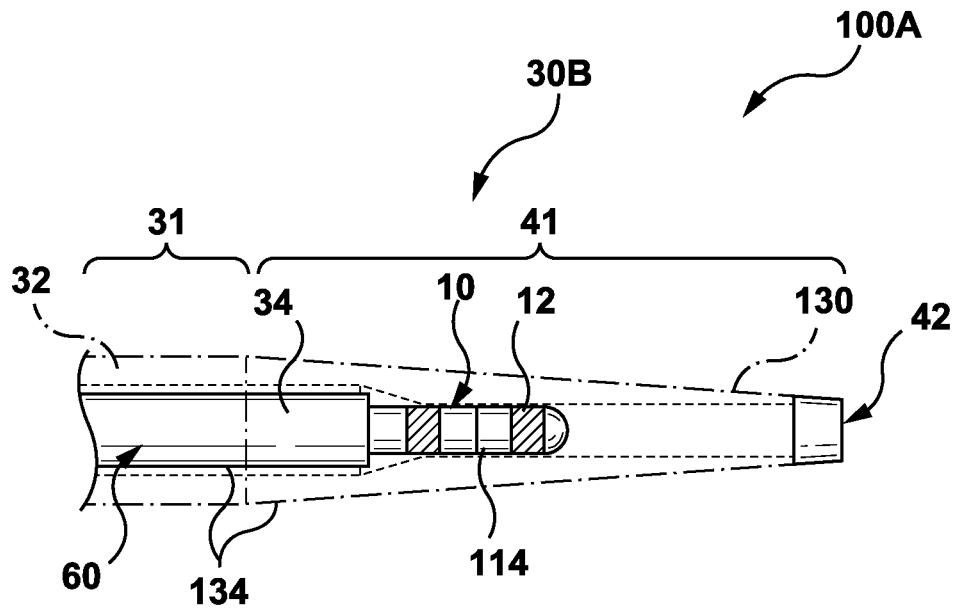
FIG. 3B shows an assembly comprising a dilator, a stylet defining a reinforcing member, and an RF wire, in a drop down position, in accordance with an embodiment of the present invention.
Figure 3C:
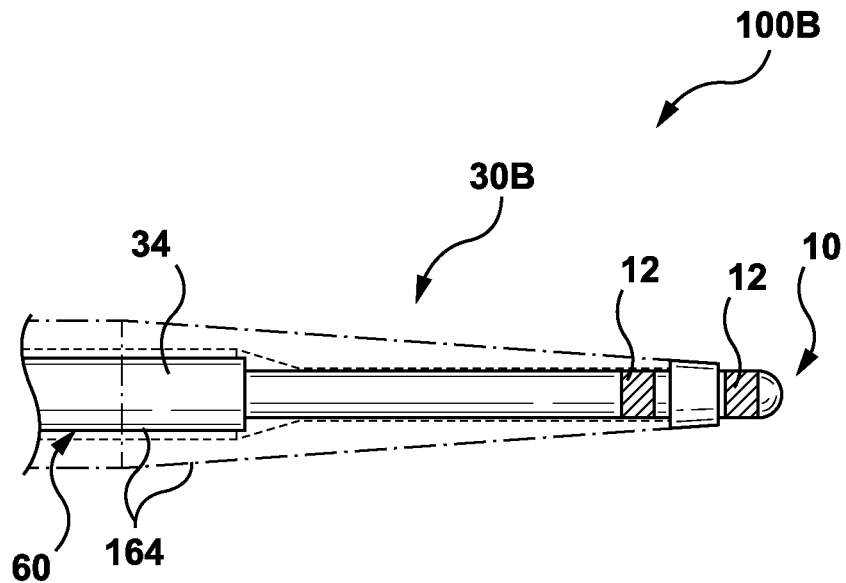
FIG. 3C shows an assembly comprising a dilator, a stylet defining a reinforcing member, and an RF wire, in an arcing position, in accordance with an embodiment of the present invention.

In some embodiments of the present invention, a substantially flexible energy based puncturing device 114 is provided (such as an RF guidewire) that comprises one or more device side radiopaque markers (or in other words one or more device radiopaque markers) at a distal end of thereof, for example, as shown in FIGS. 39 and 3C. In some such embodiments, as noted above, the supporting member 130 also comprises a supporting member radiopaque marker at the distal end of the supporting member 130 (as shown in FIGS. 1C and 1D). In some such embodiments, similar to the embodiments shown in FIGS. 39 and 3C, the one or more device radiopaque markers 12 are configured to co-operate with the supporting member radiopaque marker 42 to indicate the relative position of the substantially flexible energy based puncturing device 114 (such as an RF guidewire 10). The embodiments, shown in FIGS. 313 and 3C illustrate a dilator 30B that is provided separately from a stylet 64. However, in alternative embodiments as described currently the stylet 64 may be a reinforcing mean 34 that is provided within a dilator 30A.

In some such embodiments, the assembly 100 comprises an initial configuration 100A, where the substantially flexible energy based puncturing device 114 (such as an RF guidewire 101 is positionable within the supporting member 130 such that the one or more device radiopaque markers 12 are not in alignment with the supporting member 130 radiopaque marker 42, as shown in FIG. 3A. In some such examples, multiple radiopaque markers may be visible under imaging, including the one or more device radiopaque markers 12 and the supporting member radiopaque marker 42.

In some such examples, the assembly 100 comprises a first configuration 100B, as shown in FIG. 313 where the substantially flexible energy based puncturing device 114 (such as an RF guidewire 10) is positionable within the supporting member 130 such that the one or more device radiopaque markers 12 are in alignment with the supporting member 130 radiopaque marker 42, as Shown in FIG. 3B, in some such examples, a single radiopaque marker may be visible under imaging [including the one or more device radiopaque markers 12 and the supporting member radiopaque marker 42 that may be arranged in close proximity to one another].

The assembly 100 additionally has a second configuration 100B, where the substantially flexible energy based puncturing device 114 (such as an RF guidewire 10) is positionable/advanceable within the supporting member 130 such that the one or more device radiopaque markers 12 are substantially not in alignment or misaligned with the supporting member radiopaque marker 42. In some such examples: the misalignment of the one or more device radiopaque markers 12 with the supporting member radiopaque marker 42 indicates positioning of an energy delivery portion 114d of the flexible energy based puncturing device 114 (such as an RF electrode tip 10d of an RF guidewire 10) beyond the supporting member (for example distal to the distal tip or end of the supporting member 130) for positioning against a target tissue site for puncture of tissue. In some such examples, similar to FIG. 3A, multiple radiopaque markers may be visible under imaging [including the one or more device radiopaque markers 12 and the supporting member radiopaque marker 42, where the one or more device radiopaque markers 12 are positioned distally 10 the supporting member radiopaque marker 42, indicating that the distal electrode tip 10d is positioned against a target tissue site (such as the septum of the heart) for puncturing the tissue.

In some such examples, the sheath 20, and dilator 30A as well as the reinforcing member 34 are all radiopaque, and have radiopaque properties to enable them to visible under imaging. In some such examples, one or more of the sheath 20, dilator 30A, and reinforcing member 34, such as a metal hypo-tube comprise radiopaque materials in addition to radiopaque markers [42]. The reinforcing member 34 such as a metal shaft or hypotube is also radiopaque. In some such embodiments, polymers forming the sheath 20 and/or the dilator 30A may comprise polymer radiopaque filler such as barium sulfate 20% so there is contrast with the one or more markers [12, 42] at the distal tip. In other words this may provide visibility under imaging and may additionally provide contrast with the one or more markers [42, 12] which may allow the user to see the dilator 30A in relation to the RF guidewire 10 under imaging, to see whether the RF guidewire 10 is positioned in or outside the dilator 30A [i.e., whether the distal segment of the RF guidewire 10 is distal to the dilator 30A]. In other examples, puncturing device 114 (such as an RF guidewire 10), sheath 20, dilator 30A, as well as reinforcing member 34 are also visible using ultrasound imaging systems, radiopaque coil 106 and markers 12 being particularly echogenic.

Supporting Member with Blunt Tip

In some embodiments of the present invention, the supporting member 130 comprises a substantially blunt distal tip or edge 143, as shown in FIG. 1A, in order to provide a substantially atraumatic distal tip 143, while providing the advantages of a substantially rigid or stiff supporting member 130 (such as by providing the reinforcing member 34) therein.

In one such embodiment, an overall method/workflow is provided that illustrates a method of carrying out a transseptal puncture procedure using an assembly 100, as described herein above. The method disclosed herein provides one or more advantages associated with an assembly comprising an energy delivery component that is provided separately from the rigid component. Details of the method are provided herein below.

Method Using Example 1

Figure 2A:
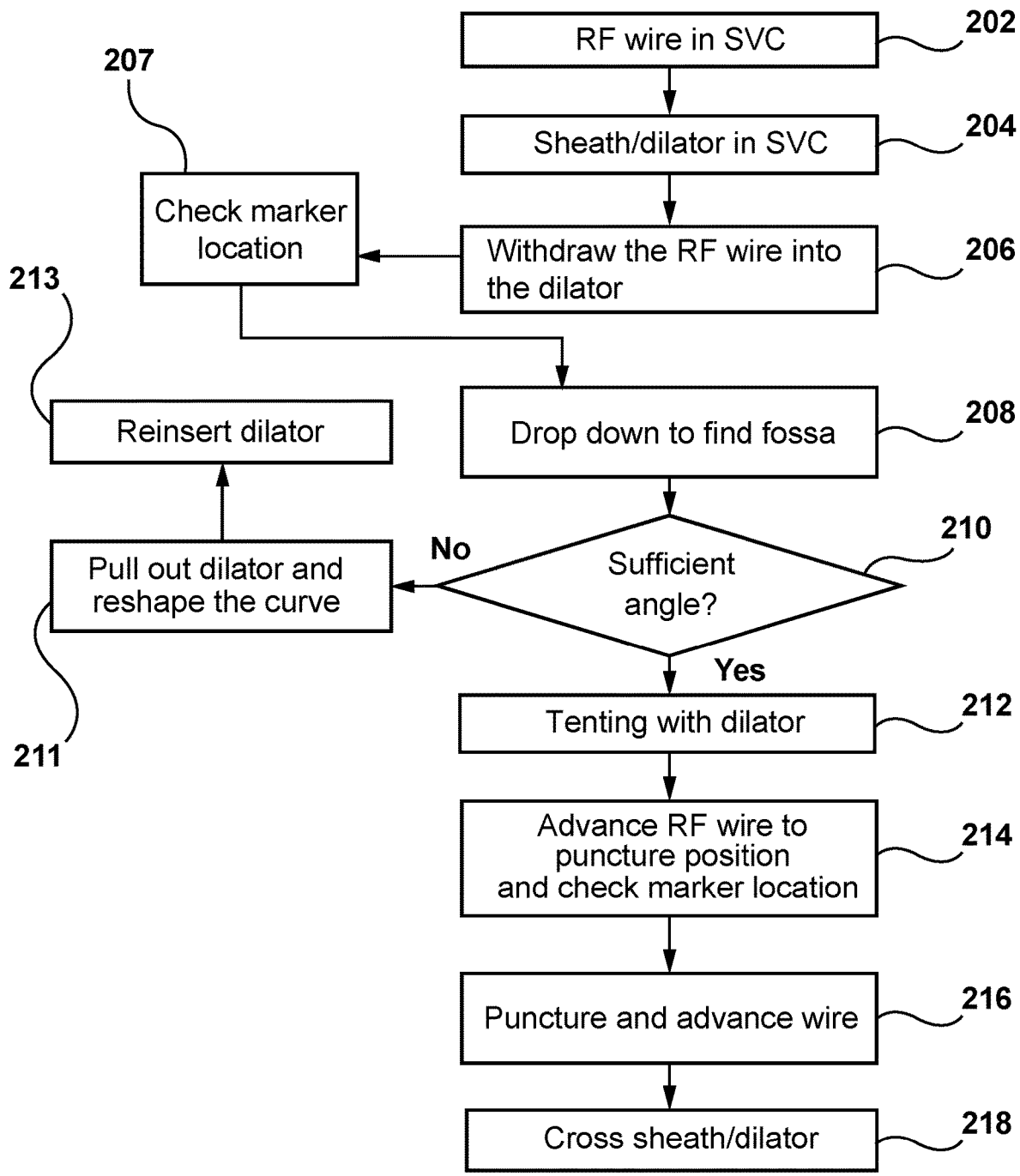
FIG. 2A is an illustration of a flow diagram showing a method of performing a transseptal procedure, in accordance with an embodiment of the present invention.
Figure 2B:
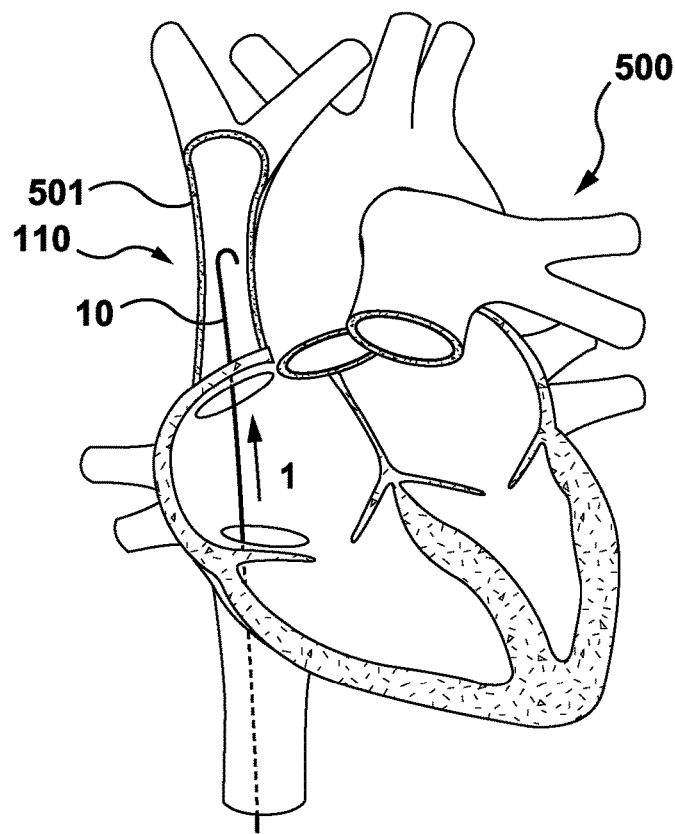
FIGS. 2B-2G illustrate steps of a method of performing a transseptal procedure, in accordance with an embodiment of the present invention.
Figure 2C:
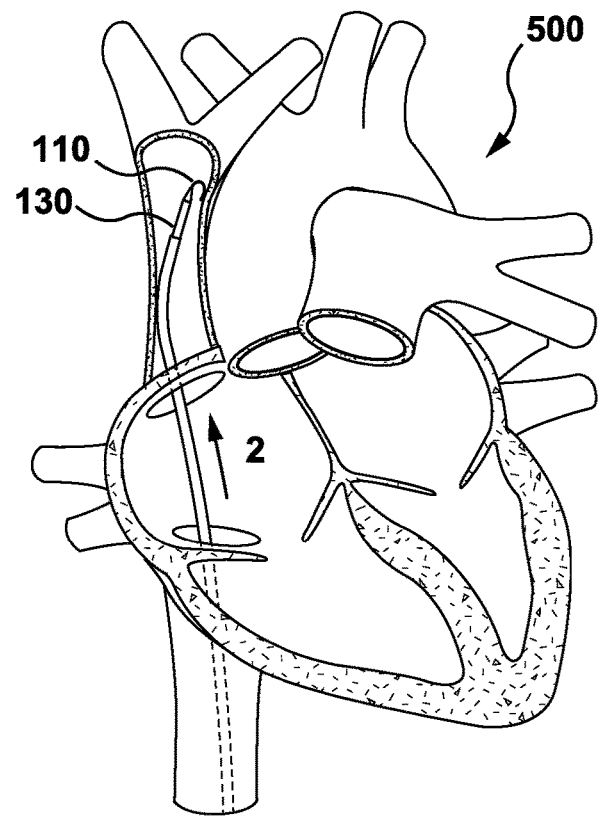
Figure 2D:
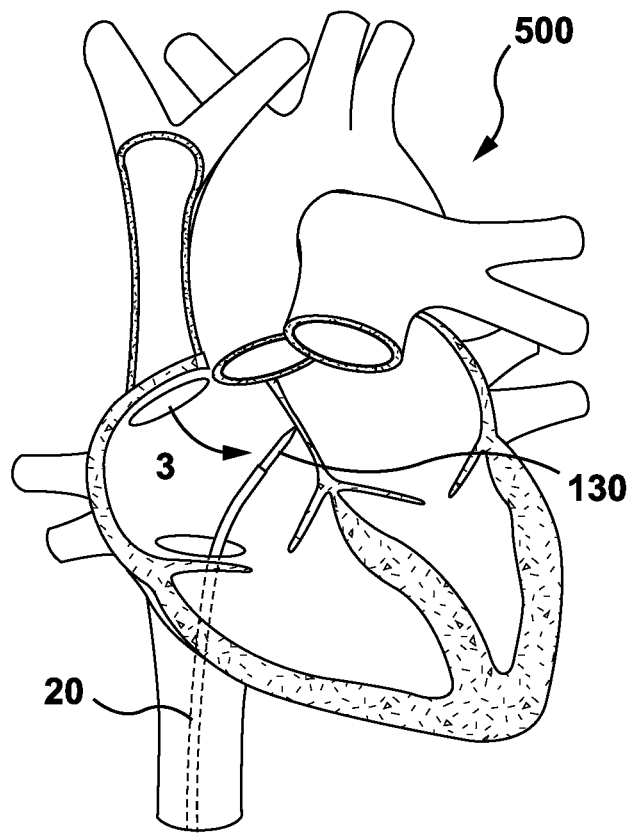
Figure 2E:
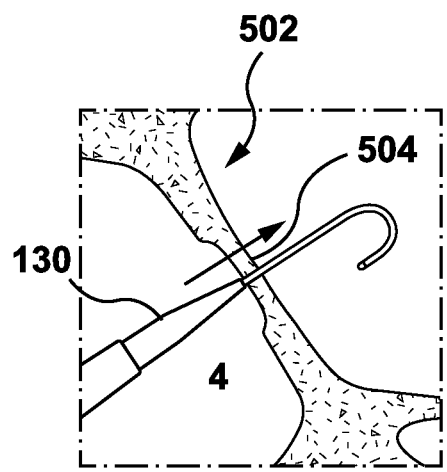
Figure 2F:
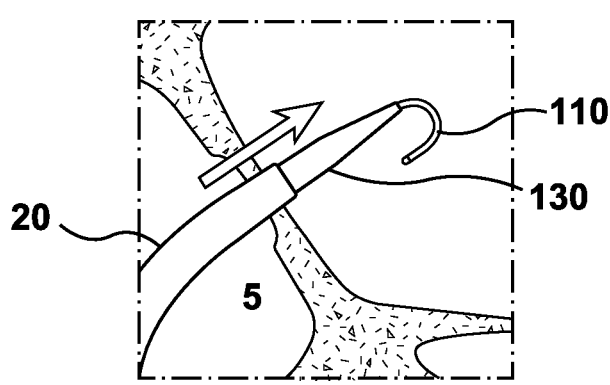

As a general overview, in one broad embodiment, with respect again to FIG. 2A-2G, a method is provided for carrying out a transseptal puncture, the method comprising: (i) Advancing the RF wire into the superior vena cava, as shown in FIG. 2B, (ii) advancing the sheath and dilator over the wire into the superior vena cava, as shown in FIG. 2C; (iii) withdrawing the RF wire into the dilator, as shown in FIG. 2D; (iv) drop down from the SVC into the heart to find the fossa, as additionally shown in FIG. 2D; (v) tenting with the dilator; (vi) advancing RF wire to puncture position, also with reference to FIG. 2D; (vii) puncturing and advancing RF wire, as shown in FIG. 2E; and (viii) crossing the sheath and dilator over the RF wire, as shown in FIG. 2F.

More specifically, in a specific embodiment of a method of the present invention, with reference again to FIG. 2A, a method is provided for carrying out a transseptal puncture procedure using an assembly 100 comprising a flexible RF wire 10, a sheath 20, and a dilator 30A, the method comprises the following steps: at step 202, [1] advancing the RF wire into the superior vena cava (SVC) to gain access, as additionally illustrated in FIG. 2B. In some such embodiments, providing the energy delivery component (flexible RF wire) separately from the reinforcing member allows the energy delivery component to be used as an access wire. More specifically, the dilator 30A can be advanced later, allowing the flexible RF wire to provide access to the SVC without the use of an additional access wire. This may help reduce the number of steps and streamline the procedure, and as such may reduce procedural time and complexity.

The method additionally comprises the following steps: at step 204, [2] advancing the sheath 20 and dilator 30A combination over the flexible RF wire into the SVC. Thus, the flexible RF wire 10 functions as an access wire and enables the sheath 20 and dilator 30A (for example as an assembly) to be tracked over the flexible RF wire 10 into the SVC as shown in FIG. 2C.

The method additionally provides: at step 206, withdrawing the RF wire into the dilator 30A. The method may optionally comprise step 207 of using proximal markers on the RF wire to determine the relative positioning between the RF wire and the sheath/dilator. For example, in the embodiment of the puncture device shown in FIGS. 5A-5C, the proximal marker may be used to determine whether the active tip of the puncture device is entirely within the dilator/sheath, or exposed from the dilator/sheath. This positioning may optionally be verified or further adjusted using visualization or mapping techniques. After confirming the relative positioning of the wire (e.g., that the wire is entirely within the sheath/dilator), the user may proceed to step 208. In step 208, the method comprises [3] performing a drop down from the SVC into the heart to locate the fossa, as shown in FIG. 2D for carrying out the step of positioning the assembly 100. In one such example, having the reinforced member 34 (within the dilator 30A) as separate from and operable independently form the flexible RF wire provides the additional advantage of allowing the drop down to be repeated if the fossa is missed in the first pass. More specifically, it eliminates the need to re-wire, in other words to re-insert an access wire, remove the access wire and then re-advance a rigid puncture device such as a needle into the SVC in order to repeat the drop down. More specifically, in an embodiment of the instant application, the dilator 30A (and thus the reinforcing member 34) may be partially removed or retracted along with the sheath 20 and the flexible RF wire 10 may be re-advanced into the SVC. The sheath 20 and the dilator 30 may then be re-advanced over the flexible RF wire 10, as shown in FIG. 2C and the drop down may be repeated to allow the RF wire 10 to engage the fossa. This may help reduce procedural time and increase safety as an additional exchange is not required. Adding an additional exchange may add more time and add unnecessary risk. Thus, procedural time and risk may be reduced with the current embodiments where the energy delivery component and the rigid component are decoupled.

The reinforcing member 34 [within the dilator 30A] provides the additional advantage of providing sufficient stiffness to the assembly 100 to facilitate the drop down, at step 208. As such the reinforcing member 34 enables sufficient force transmission and torque to allow the assembly 100 to engage the septum, as illustrated in FIG. 2D. The method further comprises: at step 212 tenting with the dilator 30A, with reference to FIG. 2D. The reinforcing member 34 provides sufficient stiffness to the assembly 100 to enable force to be imparted to the distal end of the assembly 100, thus enabling tenting with the dilator 30A. In some examples, having the reinforcing member 34 within the dilator 30A, allows it to be removed and re-shaped to allow for optimizing the position against the fossa. In some such embodiments, prior to the step of tenting, at step 210, the physician may assess whether the angle of the dilator 30A and/or the assembly 100 is sufficient. If the angle is not deemed to be sufficient, at step 211, the physician may pull out the dilator 30A and reshape the curve. The dilator may be then be reinserted as indicated by step 213. The procedure then may be repeated starting at step 208, and a drop down may be performed again using the assembly 100. Once the fossa has been located, the physician may proceed with the step of tenting with the dilator, at step 212. In some cases, it may be necessary to repeat the procedure by starting at previous steps such as steps 202, 204, or 206 before step 208 may be performed. This is because the RF wire may not be properly positioned to allow a drop down (step 208) to be performed without repositioning the assembly.

The method additionally comprises the steps of: at step 214, advancing RF wire 10 to puncture position and at step 216 [4] puncturing and advancing RF wire 10, as shown in FIG. 2E. At step 214, as the RF wire is being advanced to the puncture position (i.e., residing outside the sheath/dilator), the user may optionally visually or tactilely monitor the proximal marker on the RF wire to determine the relative positioning between the RF wire and the dilator/sheath. In one embodiment (see, e.g., FIGS. 5A-5C), as the proximal marker disappears into the handle/hub of the dilator/sheath, the user knows that the active tip of the RF wire is now exposed (i.e., in the puncture position). This positioning may optionally be verified or further adjusted using visualization or mapping techniques. At step 216, the RF wire punctures the tissue and is advanced therethrough. The advancement of the RF wire 10 into the left side of the heart 500, enables anchoring of the RF wire 10 on the left side of the heart to maintain access to the left side of the heart. The flexible RF wire 10 may provide the additional advantage of allowing the operator to push hard without injury as the flexible RF wire is more flexible. The method additionally comprises: at step 218, [5] crossing the sheath and dilator over the RF wire 10, as additionally shown in FIG. 2F. The flexible RF wire 10 may additionally protect the open end of the sheath 20/dilator 30A so it does not push hard into the tissue. At step 218, the sheath 20 and dilator 30A [including the reinforcing component 34] may then be removed.

Figure 2G:
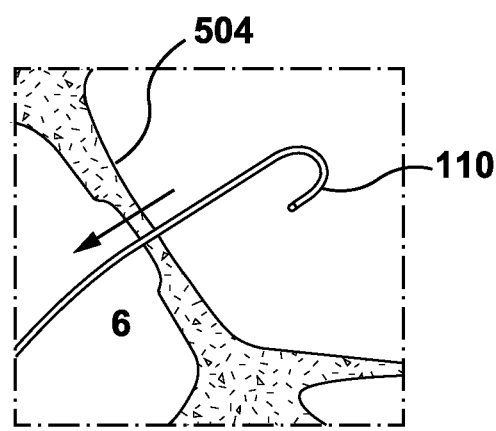

As outlined herein, energy delivery component is provided as a flexible RF wire 10 that is separate from a stiff component such as a reinforcing member 34 [provided within the dilator 30A], where the reinforcing member 34 [with the dilator 30A] is separable from and removable from the flexible RF wire 10. This provides the additional advantage, in that the reinforcing member 34 [within dilator 30A] may be removable after transseptal puncture and access, providing a step [6] of allowing the flexible RF wire 10 to remain positioned within the left atrium which allows for immediate anchoring of the flexible RF wire within the left atrium, as shown in FIG. 2G. In one such example, the RF wire may be positioned within the left superior pulmonary vein for anchoring. This may enable the RF wire to maintain access into the left atrium, allowing removal of the reinforcing member 34 [along with dilator 30A to facilitate exchange of devices into the left atrium using the flexible RF wire. This may additionally reduce an additional exchange of the left side as it may eliminate the need for the physician to advance another wire after puncture to maintain access on the left side for tracking additional devices into the left side. An additional benefit of minimizing exchanges on the left side, in addition to reducing procedural time and the number of steps required, is minimizing risk of infection, embolisms and stroke. In another example, the RF wire 10 may have a pigtail curve at the distal end. This may enable anchoring of the RF wire 10 in the left atrium instead of the pulmonary vein. Alternatively, the RF wire 10 may be used to anchor in the pulmonary vein. In some such examples, the former method of anchoring in the left atrium may provide additional advantages not found in the latter method.

Using the Proximal Markers on the Puncture Device

In some embodiments of the method, the user positions the puncture device relative to the supporting member using the proximal marker 116 without using an imaging system such a fluoroscopy in a step that can be called, 'macro-positioning'. Subsequent to the 'macro-positioning', the user may utilize an imaging system (e.g. fluoroscopy) for more precise positioning of the RF guidewire relative to the introducer and the target tissue in a step that can be called micro-positioning. By using the proximal and distal markers, a user can perform the early part of positioning the apparatus without fluoroscopy to thereby reduce the amount of X-rays the user and patient are exposed to when compared to performing the entire procedure under fluoroscopy. In some alternative embodiments of the method, the part of the procedure involved with positioning the puncture device relative to the supporting member is performed without any fluoroscopy.

Using the Same Device for Initial Track Up/Access and Positioning

In some embodiments of the present invention, with reference now to FIGS. 2A-2G, a method is disclosed for puncturing tissue. The method comprises the step of: [1] accessing a region of tissue within a patient's body by advancing a device (such as a puncture device 110 which may be an RF guidewire 10) into the region of tissue, as shown in FIG. 2B. In some such examples the method of puncturing a region of tissue comprises a method of carrying out a transseptal puncture where the step of accessing the region of tissue comprises advancing the device (such as the puncture device 110) into the superior vena cava (SVC) 501 adjacent a heart 500 of the patient.

In some embodiments of the present invention, the method for puncturing tissue additionally comprises the step of: [3] positioning a device at a target tissue site in the region of tissue, as shown in FIG. 2D, by for example: [2] first tracking a supporting member 130 (such as reinforced dilator 30A) over the puncture device 110 to support the device (such as puncture device 110) as shown in FIG. 2C, to [3] enable advancement of the device (such as a puncture device 110) towards a target tissue site in order to position the device at the target tissue site for puncturing, as shown in FIG. 2D.

In some such examples, the step of positioning the puncture device 110 at the target tissue site comprises performing [3] a drop down from the superior vena cava (SVC) into the heart 500 of the patient to locate a fossa ovalis (or in other words fossa) 504 along a septum 502 of the heart 500, by first for example (2) tracking or advancing a supporting member 130 (such as a dilator 30A) over the device (such as a puncture device 110) into the SVC to (3) facilitate the drop down to position the puncture device 110 at the fossa 504.

In some such examples, as shown in FIGS. 2B-2D, the steps of accessing [1], as shown in FIG. 2B and positioning [3], as shown in FIG. 2D, are performed using the same device such as a puncture device 110, wherein the puncture device 110 is usable without the supporting member 130 during the step of accessing [1] and wherein the device is usable with the supporting member 130 during the step of positioning [3].

Using a Puncture Device for Initial Access and Positioning

In some such embodiments of the present invention, as shown in FIGS. 2B-2D, the steps of accessing and positioning are performed using a puncture device 110.

Using the Same Device for Initial Access, Positioning and Puncturing

In some such embodiments of the present invention, as shown in FIG. 2E, the method additionally comprises: [4] a step of puncturing through the target tissue site using a device (such as the puncture device 110) after the step of positioning [3] as shown in FIG. 2D. The supporting member 130 supports the device (such as puncture device 110) during puncturing [4] where the steps of accessing [1], positioning [3] and puncturing [4] are performed using the same device.

In some embodiments of the present invention, the step [4] of puncturing through the target tissue site comprises the step [4] of puncturing through the fossa 504 to gain access to a left side of the heart 500. This enables one or more devices of the assembly 100, such as the supporting member 130 (such as dilator 30A) and sheath 20 of the assembly 100 to be tracked over the RF guidewire 10 into the left side of the heart.

Using a Puncture Device for Initial Access, Positioning and Puncturing

In some such examples, as shown in FIGS. 2B-2E, the steps of accessing, positioning, and puncturing are performed using a puncture device 110.

Using the Same Device for Initial Access, Positioning and Puncturing and Anchoring In accordance with an embodiment of the present invention, the method additionally comprises a step of anchoring, as shown in FIG. 2E, where the step of anchoring is performed using a device (such as the puncture device 110) after the step of puncturing [4] through the target tissue site, to maintain access through the target tissue site to the other side of the target tissue site, to allow one or more additional device [such as sheath 20 and the supporting member 130 comprising the dilator 30A] to be tracked over the device (such as the puncture device 110) to the other side of the target tissue site, as shown in FIG. 2F, where the steps of accessing, positioning, puncturing and anchoring are performed using the same device. The puncture device 110 such as the RF guidewire may be left to maintain access to the left side of the heart, as shown in FIG. 2G. The supporting member 130 for example comprising the dilator 30A may be removed or retracted to allow anchoring using the RF guidewire 10. The RF guidewire 10 functions as a rail to guide one more devices to the left side of the heart. In some such examples, the RF guidewire 10 provides a substantially stiff rail to guide the one or more devices to left side of the heart while being substantially atraumatic to minimize damage to the tissue.

In some such embodiments of the present invention, the step of anchoring to maintain access through the target tissue site comprises advancing the device (such as the puncture device 110) through the fossa to the left side of the heat to maintain access to the left side of the heart. The step additionally comprises a step of removing the supporting member 130 [such as dilator 30A] and leaving the puncture device 110 [such as RF guidewire 10] to maintain access to the region of tissue such as the left side of the heart.

As such, in some examples, the step of anchoring comprises removing the supporting member 130 comprising the dilator 30A to enable anchoring by allowing the RF guidewire 10 to remain positioned to maintain access to the eft side of the heart. The sheath 20 may additionally be removed as well.

Alternatives for the Device being Used for Initial Access, Positioning and/or Puncturing—Based on the Base Claim these Dependents Depend from In some such embodiments of the present invention, the device comprises a flexible puncture device 112 where one or more of the steps of accessing, positioning, puncturing and anchoring are performed using the flexible puncture device 112. In some such examples, each of the steps of accessing, positioning, puncturing and anchoring are substantially performed using the flexible puncture device 112.

In some such embodiments of the present invention, the device comprises a substantially flexible guidewire (such as a mechanical guidewire 118 or an RF guidewire 10) where one or more of the steps of accessing, positioning, puncturing and anchoring are performed using the substantially flexible guidewire (such as a mechanical guidewire 118 or an RF guidewire 10). In some such examples, each of the steps of accessing, positioning, puncturing and anchoring are substantially performed using substantially flexible guidewire (such as a mechanical guidewire 118 or an RF guidewire 10).

In some such embodiments of the present invention, the device comprises a flexible energy based puncture device 114 where one or more of the steps of accessing, positioning, puncturing and anchoring the steps are performed using the flexible energy based puncture device 114. In some such examples, each of the steps of accessing, positioning, puncturing and anchoring are substantially performed substantially using flexible energy based puncture device 114.

In some such embodiments of the present invention, the device comprises a flexible RF guidewire and wherein one or more of the steps of accessing, positioning, puncturing and anchoring are performed using the flexible RF guidewire 10. In some such examples, each of the steps of accessing, positioning, puncturing and anchoring are substantially performed substantially using flexible the flexible RF guidewire 10.

In some such embodiments of the present invention, wherein the device comprises a flexible mechanical guidewire 118 having a relatively sharp distal tip 118d wherein one or more of the steps of accessing, positioning, puncturing and anchoring are performed using the flexible mechanical guidewire 118. In some such examples, each of the steps of accessing, positioning, puncturing and anchoring are substantially performed substantially using flexible mechanical guidewire 118.

Repeating Steps of Accessing and Positioning

In some such embodiments of the present invention, the method further comprises repeating the steps of accessing [1], shown in FIG. 2B, and positioning [3] as shown in FIG. 2D, until the device (such as the puncture device 110) is positioned at the desired target tissue site prior to the step of puncturing [4], as shown in FIG. 2E.

Reshaping the Supporting Member

In some such examples, repeating the step of positioning [3] as shown in FIG. 2D, further comprises reshaping a curvature of the supporting member 130 after removing the supporting member 130, and re-tracking [2] the supporting member 130 over the device, as shown in FIG. 2C (such as the puncture device 110 that has been re-positioned [1] within the SVC as shown in FIG. 2B), prior to repeating the step of positioning as shown in FIG. 2D, which in the example shown comprises a drop-down procedure to find the fossa 504. In a specific example, the supporting member 130 comprises a reinforcing member 34, where the step of positioning is performed using the reinforcing member 34.

In some such embodiments of the present invention, the method comprises reshaping the supporting member 130 (such as the reinforced dilator 30A). In some such examples, the method comprises pulling the dilator element or dilator 30A out and reshaping it. In other examples, comprises pulling both the dilator element 30A and the sheath 20 out and reshaping it.

Supporting Member Comprises Reinforced Dilator

In some such examples re-shaping is performed using the supporting member 130 comprising a reinforced dilator 30A where the reinforced dilator 30A comprises the reinforcing member 34, where the step of positioning is performed using the reinforced dilator 30A that can be re-shaped.

Supporting Member Comprises a Stylet

In some embodiments, alternatively, as discussed further herein below, with respect to FIGS. 4A-4E, the step of re-shaping can be performed using the supporting member 130 comprising a stylet 60 wherein the stylet 60 is the reinforcing member 34, and the step of positioning is performed using the stylet 60.

In some such examples, the stylet element 60 can be taken out and reshaped. In other examples, the stylet element 60 along with the sheath 20 and/or dilator 30B may be pulled out and re-shaped to see what the net shape might be and then can be re-inserted therein.

The methods outlined herein above may also be used for embodiments discussed further herein below having a removable stylet 60, as shown in FIGS. 4A-4E.

Mapping System to Visualize Initial Access Tracking and Positioning

In some such embodiments with respect to FIGS. 2A-2G, and also additionally with reference to embodiments shown in FIGS. 4A-4E, the step of positioning is performed using a flexible RF guidewire 10. In some such examples, the steps of positioning, and puncturing are performed using a flexible RF guidewire 10. Still additionally, in some such examples, the steps of positioning, puncturing, and anchoring are performed using a flexible RF guidewire 10. In some such examples, a mapping system as provided below may be used to visualize the steps of positioning, and anchoring. In some such examples, as provided in FIGS. 2A-2G and FIGS. 4A-4E, the step of accessing may additionally be performed using the RF guidewire 10. As such, in some such examples, a mapping system as provided below may be used to visualize the flexible RF guidewire 10 using a mapping system during the steps of accessing positioning, and anchoring. In some such examples, the method further comprises the step of visualizing the flexible RF guidewire 10 using a mapping system during the steps of accessing and positioning.

As such embodiments of the present invention provide a mapping system that is usable to visualize an RF guidewire 10 during a method of puncturing tissue during one or more of the steps of accessing, positioning, and anchoring.

In some instances, the mapping device comprises an electro-anatomical mapping system where the electro-anatomical mapping system may be magnetic or impedance based to create virtual volumes. In some examples, the electro-anatomical mapping system is usable with other echocardiographic imaging modalities, which may be ultrasound. The echocardiographic imaging modalities may be used as an overlay in maps, in other words they may be used provide additional information to the mapping system. The echocardiographic imaging modalities may comprise intracardiac cardiography or FEE echorcardiographic In some examples, the method involves switching between a mapping mode that is used for each of the steps of accessing, positioning, and anchoring and the puncture mode that is used for the step of puncturing.

In some such examples, the method of mapping the RF guidewire 10 to visualize using an imaging modality, may be usable with a flexible wire with an electrode which may or may not deliver energy which may be used for recording purposive. In some cases it may be a passive electrode for recording purposes. Alternatively as discussed above, if an RF guidewire 10 is used, then the mapping system is usable with an active electrode such as the distal electrode tip 10d of the RF guidewire 10. As such the recording and mapping properties of a mapping system, are usable with a guidewire having a passive electrode or an active electrode. In a specific example, where a wire is provided with a passive electrode for mapping, the wire may comprise a puncturing means or a means to puncture tissue. In one instance the wire may comprise a mechanical guidewire 118 that may have a sharp distal tip 118d for puncturing tissue.

In some such embodiments the reinforcing member is the stylet 60 that is usable independently from the substantially flexible energy based puncture device 114 such as an RF wire 10.

Example 2

In another example, embodiments of the present invention provides an assembly 300, as shown in FIG. 3A, for puncturing tissue (such as creating a transseptal puncture through a septum of a heart) Similar to embodiments described herein above, the assembly 300 provides a puncture device such as a substantially flexible energy delivery puncture device 114 for puncturing tissue via delivery of energy (such as flexible RF guidewire 10 and a supporting member for supporting the substantially flexible energy delivery puncture device, such as a separate reinforcing member 34. In some such examples, the supporting member comprises a reinforcing member 34. In some such embodiments, the substantially flexible energy delivery puncture device 114 (such as RF guidewire 10) is capable of being selectively insertable within the supporting member 130 to be selectively usable in co-operation therewith during a portion of the procedure and wherein the substantially flexible energy delivery puncture device 114 (such as RF guidewire 10) is usable independently therefrom during another portion of the procedure, in order to facilitate exchange and positioning while providing substantially atraumatic puncture of tissue.

Overall Assembly

In one such example, as illustrated in FIG. 3A, the assembly 300 comprises a flexible energy delivery component 114 that is provided separately from and is operable independently from a supporting member. In one such example, the flexible energy delivery component comprises an RF wire 10, and the separate supporting member 130 comprises a stylet 60 that defines a reinforcing member 34. In other words, as provided herein below the supporting member 130 is the reinforcing member 34 that is provided as a stylet 60 that is usable independently from a puncture device 110 such as a flexible puncture device 112. In still others words, the supporting member 130 is defined by the reinforcing member 34, where in one example, the reinforcing member 34 comprises the stylet 60. The assembly 300 additionally comprises a sheath 20 and a dilator 30B that are usable with the flexible RF wire 10. In the particular example shown the reinforcing member 64 is also provided separately from and removable from the dilator 30B which in the present embodiment is provided as a flexible dilator.

Some such embodiments comprises a dilator 30B that is usable with the supporting member 130 to form a supporting member assembly 134 or selective use there with during a portion of the procedure, as shown in FIG. 3B. In some such embodiments, as noted above, the supporting member 130 comprises a stylet 60 defining the reinforcing member 34. In some examples, a dilator 30B is provided that is usable with the stylet 60 for selective use there-with to form a stylet assembly 164, as shown in FIG. 3C.

In some such embodiments, the puncture device 110 comprises a substantially flexible energy based puncture device 114. In a specific instance of this example, the substantially flexible energy based puncture device 114 comprises a flexible RF guidewire or wire 10. In some embodiments, the RF guidewire 10 is capable of being selectively usable in co-operation with the stylet 60 (for example by being selectively being coupled thereto) during a portion of the procedure, and the RF guidewire 10 is usable independently from the stylet 60 during another portion of the procedure. Where selective use of the RF guidewire 10 in conjunction with the stylet, as well as without the stylet 60, facilitates puncture of tissue.

Supporting Member/Reinforcing Member Shape-Ability

In some such embodiments of the present invention where the supporting member 130 is provided separately from a dilator 30B, the assembly 300 provides a supporting member 130 that is shapeable to enable it to be removed from the puncture device 110 (such as a flexible tissue puncture device 112, for e.g. a substantially flexible energy based tissue puncture device 114) to enable a curve of the supporting member 130 be re-shaped to be reinserted therewith. For example, the re-shaped supporting member 130 is re-insertable with and/or usable with the substantially flexible energy based tissue puncture device 114 and/or one or more other components of the assembly 300 such as dilator 30B and/or sheath 20), in order to optimize the position of the assembly 300 against a target tissue site to facilitate puncture (such as a fossa of the heart to facilitate a transseptal puncture).

In a specific example, the stylet 60 is shapeable to enable the stylet 60 to be removed from the substantially flexible puncture device to enable a curve of the stylet 60 be re-shaped to be reinserted therewith, in order to optimize the position of the assembly against a target tissue site. In some such examples, the stylet 60 is removable from the one or more components or member of the assembly 300 to be re-shaped to be re-inserted therewith to position the assembly 300 at the target tissue site.

Details of the stylet 60 defining the reinforcing member 34 in use with a dilator 30B and flexible RF wire 10 are shown in FIGS. 3B and 3C. More specifically, FIGS. 3B and 3C, illustrate a dilator 30B which in some examples is a flexible dilator such as a standard transseptal dilator without having a reinforcing member embedded therein or in other words separately from the dilator 30B, the dilator 30B comprising a proximal portion 31 that terminates at a distal tip 41. In some embodiments, the dilator 30B may additionally include a radiopaque marker 42 at the distal tip 41. Similar to embodiments disclosed herein above, the dilator 30B comprises a dilator shaft 32 that extends along the proximal portion 31. However, unlike embodiments discussed herein above, assembly 300 provides a reinforcing member or component 34 defined by stylet 60 that is provided separately from the dilator 30B, and functions as a removable reinforcing member that is removable from the dilator 30B. As such, the reinforcing member 34 is provided separately from and is removable from both the flexible RF wire 10 and the dilator 30B. FIG. 3B shows the assembly 300 in position for a drop down, whereas FIG. 3C shows the assembly 300 in position for arcing to enable the transseptal puncture.

Atraumatic Stylet

In some embodiments, the stylet 60 is provided as a substantially atraumatic stylet 68, as shown in FIG. 5F to prevent damage to the dilator 30A that it is inserted in. In some such examples, the stylet 68 comprises a tapered distal tip 69 to prevent and/or help minimize skiving and to provide a smoother feel for the user upon insertion into a dilator during use.

In some embodiments, as an alternative or in addition to providing a tapered distal tip 69, the stylet 60 is made substantially atraumatic by providing a lubricous coating 67 on the stylet 60 in order to prevent and/or help minimize skiving and to provide a smoother feel for the user upon insertion into a dilator during use.

In some such examples, the lubricous coating 67 comprises a PTFE coating. The PTFE coating may be spray coated onto the stylet 60 or it may be provided as a heat shield.

Alignment Using Radiopaque Markers

In some embodiments of the present invention, similar to embodiments discussed previously with respect to assembly 100, the assembly 300 comprises a substantially flexible energy based puncturing device 114 (such as the RF guidewire 10) that comprises one or more device radiopaque markers 12 at a distal end of thereof. Additionally, the supporting member assembly comprises one or more supporting assembly radiopaque markers 42 at the distal end of a supporting member assembly 134 (for example comprising a separate reinforcing member 34 such as a stylet 60 and a puncture device 110 such as a substantially flexible energy based puncturing device 114. In one such example, the supporting assembly radiopaque marker 42 is provided on the dilator SOB of the supporting member assembly 134. In some such examples, the one or more device radiopaque markers 12 are configured to co-operate with the supporting assembly radiopaque marker 42 to indicate the relative position of the substantially flexible energy based puncturing device 114.

In some such embodiments, the assembly 300 comprises an initial configuration 100A, where the substantially flexible energy based puncturing device 114 (such as an RF guidewire 10) is positionable within the supporting member assembly 134 such that the one or more device radiopaque markers 12 are not in alignment with the supporting assembly radiopaque marker 42, as shown in FIG. 3A. In some such examples, multiple radiopaque markers may be visible under imaging, including the one or more device radiopaque markers 12 and the supporting member radiopaque marker 42.

The assembly 300 additionally has a first configuration 100B, where the substantially flexible energy based puncturing device 114 is positionable within the supporting member assembly 134 such that the one or more device radiopaque markers 12 are in alignment with the supporting assembly radiopaque marker 42. In some such examples, a single radiopaque marker may be visible under imaging [including the one or more device radiopaque markers 12 and the supporting member radiopaque marker 42 that may be arranged in close proximity to one another].

The assembly 300 additionally has a second configuration 100B, where the substantially flexible energy based puncturing device 114 (such as RF guidewire 10) is positionable/advanceable within the supporting member assembly 134 such that the one or more device radiopaque markers 12 are substantially not in alignment/misaligned with the supporting assembly radiopaque marker 42. In some such examples, the misalignment of the one or more device radiopaque markers 12 with the supporting assembly radiopaque marker 42 indicates positioning of an energy delivery portion 114 (such as electrode distal tip 10*d* or also referred to as distal electrode tip 10*d*) of the flexible energy based puncturing device 114 (such as an RF guidewire 10) beyond the supporting member assembly 134 (for example distal to the distal tip or end of the supporting member 130) for positioning against a target tissue site for puncture of tissue.

With reference now to FIG. 3A, similar to embodiments Shown in FIG. 3A and discussed previously, multiple radiopaque markers may be visible under imaging, including the one or more device radiopaque markers 12 and the supporting member radiopaque marker 42, where the one or more device radiopaque markers 12 are positioned distally to the supporting member radiopaque marker 42, indicating that the distal electrode tip 10*d* is positioned against a target tissue site (such as the septum of the heart) for puncturing the tissue.

In some embodiments of the present invention, one or members or components of the assembly 300 may be radiopaque to facilitate visualization of the assembly 300. In one such example, the sheath 20 and/or the dilator 30B comprise a radiopaque polymer and the stylet 60 (for example comprising a metal shaft) is radiopaque. As such, in some examples, the stylet 60, sheath 20 and/or the dilator 30B are all radiopaque and thus have radiopaque properties. In a specific example, the polymers forming the sheath 20 and/or dilator 30B comprise radiopaque filler such as barium sulfate 20% to provide contrast with the one or more markers 12, 42 at the distal tip, in order to allow the user to see the sheath 20 and/or the dilator 30B in comparison to the RF guidewire 10. As such, the present configuration may enhance visibility and may allow the user to ascertain when the RF guidewire (more specifically the electrode distal tip 10*d* of the RF guidewire 10) is positioned inside or whether it extends outside or beyond the distal tip of the dilator 30B.

In some embodiments of the transseptal assembly 300, the sheath 20 comprises a standard transseptal sheath, the dilator 30B comprises a standard flexible dilator and the flexible RF wire 10 is provided as a 0.035" wire. In some such examples, the flexible RF wire 10 may be J-tip wire or a pigtail wire. In one particular example, the dilator 30 comprises HDPE. The dilator 30 defines an inner diameter that is sufficient to accommodate the stylet 60. In one example, the stylet 60 that defines the reinforcing member 3 4 comprises a hypo-tube such as a metal hypo-tube. In a specific example, the stylet 60 comprises a metal hypo-tube that comprises a stainless steel hypotube. In one such example, the stainless steel hypo-tube has an ID of greater than about 0.035".

In some examples, the steerable sheath 20 may be an 8 French (Fr) steerable sheath. Alternatively, an 8.5 Fr steerable sheath 20 may be provided. In some such examples, the steerable sheath 20 may be provided with different curvatures. In a specific example, steerable sheaths 20 may be provided in different curvatures, specifically at angles of: 37, 45, 55, 90, or 135 degrees. In a specific instance of this example, the sheath tubing comprises an inner PTFE liner, a braid and a Pebax outer jacket. In some such embodiments, an 8 French (Fr) dilator 30B is provided that is compatible with an 8 French (Fr) Sheath. Alternatively, an 8.5 (Fr) dilator 30B may be provided that is compatible with an 8 French (Fr) steerable sheath 20. Some such dilators may be provided with a 64 degree curvature and an HDPE shaft. The stylet 60 may be provided as a metal hypotube. In one such instance, the stylet 60 may have an ID of greater than about 0.038" and an OD that is less than about 0.060". The dilator 30A may be provided with a 50 degree or 86 degree curvature. In some examples, materials may include HDPE and a metal hypotube that forms the reinforcing member 34. In some such examples, the RF wire 10 comprises a 0.035" OD wire and may be a J-tip wire or a pigtail wire. In a specific instance of this example, the RF wire 10 may comprise a stainless steel core with a PTFE coating.

Method [Example 2—Removable Stylet]

Using the Same Device for Initial Track Up/Access and Positioning

Figure 4A:
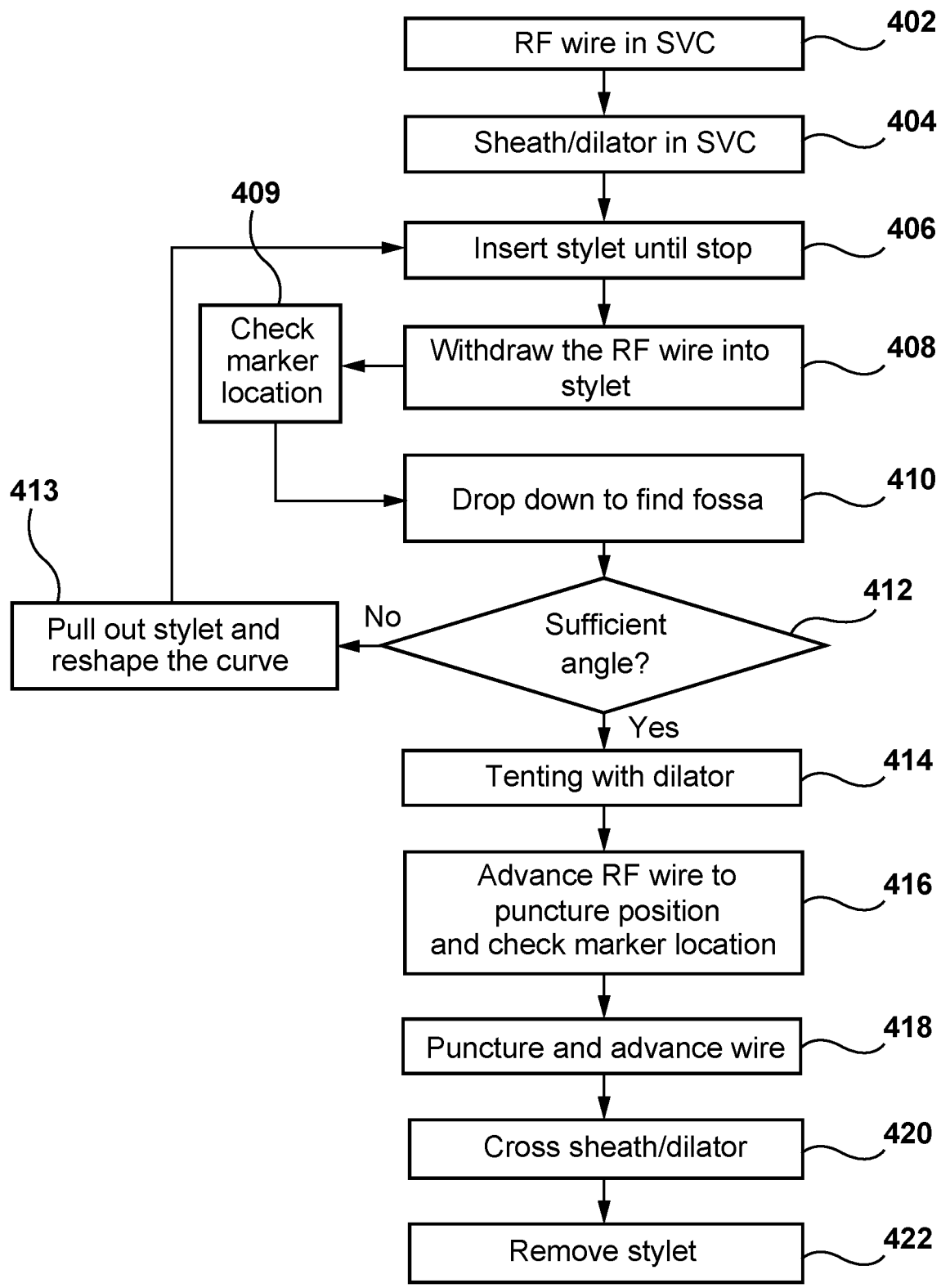
FIG. 4A is an illustration of a flow diagram showing a method of performing a transseptal procedure, in accordance with an alternate embodiment of the present invention.
Figure 4D:
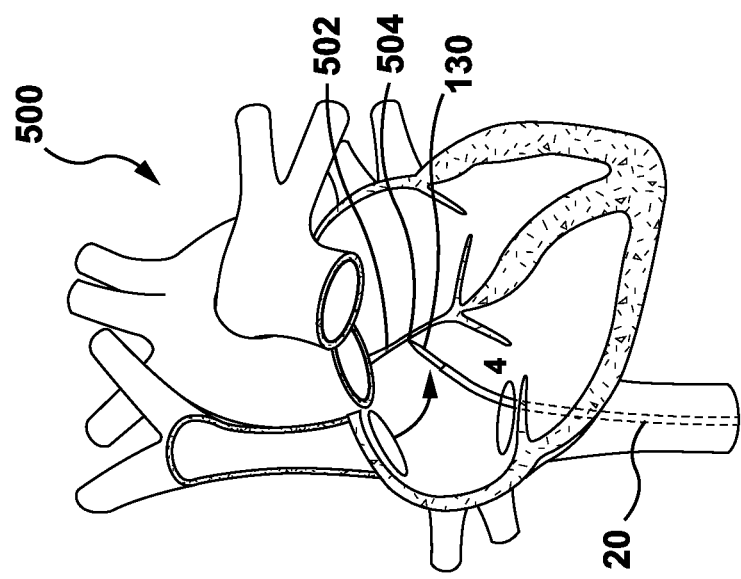
FIGS. 4B-4G illustrate steps of a method of performing a transseptal procedure, in accordance with an alternate embodiment of the present invention.
Figure 4C:
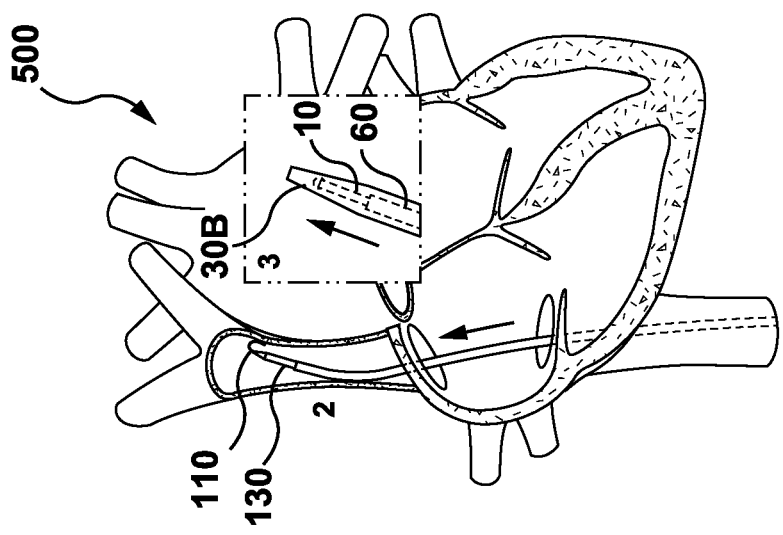
Figure 4B:
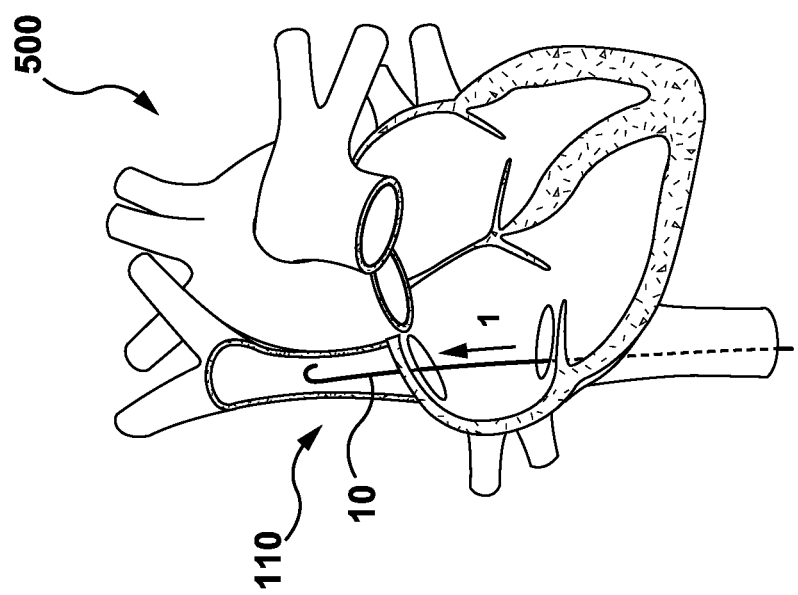

In some embodiments of the present invention, with reference now to FIGS. 4A-4G, a method is disclosed for puncturing tissue. The method comprises the step of: [1] accessing a region of tissue within a patient's body by advancing a device (such as a puncture device 110 such as an RF guidewire 10) into the region of tissue, as shown in FIG. 4B. In some such examples the method of puncturing a region of tissue comprises a method of carrying out a transseptal puncture where the step of accessing the region of tissue comprises advancing the device (such as the puncture device 110) into the superior vena cava (SVC) 501 adjacent a heart 500 of the patient, as shown in FIG. 4B In some embodiments of the present invention, the method for puncturing tissue additionally comprises the step of: [4] positioning a device at a target tissue site in the region of tissue, as shown in FIG. 4D, by for example: [3] first tracking a supporting member 130 over the puncture device 110 to support the device (such as puncture device 110) as shown in FIG. 4C, to [4] enable advancement of the device (such as a puncture device 110) towards a target tissue site in order to position the device at the target tissue site for puncturing, as shown in FIG. 4D.

In some such examples, the step of positioning the puncture device 110 at the target tissue site comprises performing [4] a drop down from the superior vena cava (SVC) into the heart 500 of the patient to locate a fossa ovalis (or fossa) 504 along a septum 502 of the heart 500, by first for example (3) tracking or advancing a supporting member 130 (such as a stylet) over the device (such as a puncture device 110) into the SVC to (3) facilitate the drop down procedure, as shown in FIG. 4D, to position the puncture device 110 at the fossa. For example, this involves dropping down the assembly 300 from the superior vena cava into the heart to find the fossa.

In some examples, the step of positioning [4] is performed by first for example additionally comprises a step of advancing [2] a sheath 20 and dilator 30B over the device (such as RF guidewire 10) into the superior vena cava, prior to tracking and advancing a supporting member 130 which may comprise inserting a stylet 60 in the dilator 30B [for example until it reaches a stop], as shown in FIG. 4C. In some such examples, the step of positioning [4] is performed after a step of withdrawing the RF guidewire into the stylet 60.

In some such examples, as shown in FIGS. 4B-4D, the steps of accessing [1], as shown in FIG. 4B and positioning [4], as shown in FIG. 4D, are performed using the same device such as a puncture device 110, wherein the puncture device 110 is usable without the supporting member 130 [comprising the stylet 60] during the step of accessing [1] and wherein the device is usable with the supporting member 130 [comprising the stylet 60] during the step of positioning [4].

Using a Puncture Device for Initial Access and Positioning

In some such embodiments of the present invention, as shown in FIGS. 4B-4D, the steps of accessing and positioning are performed using a puncture device 110 [such as an RF guidewire 10].

Using the Same Device for Initial Access, Positioning and Puncturing

Figure 4E:
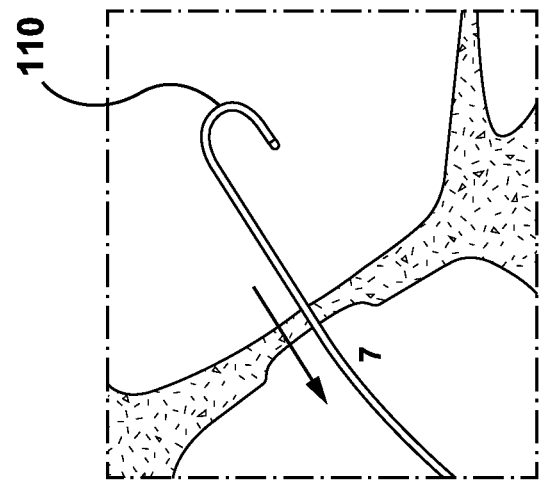

In some such embodiments of the present invention, as shown in FIG. 4E, the method additionally comprises: a step of puncturing[5] through the target tissue site using a device (such as the puncture device 110) after the step of positioning [4] as shown in FIG. 4D. The supporting member 130 [comprising the stylet 60] supports the device (such as puncture device 110) during puncturing [5] where the steps of accessing [1], positioning [4] and puncturing [5] are performed using the same device.

In some embodiments of the present invention, the step [5] of puncturing through the target tissue site comprises the step [5] of puncturing through the fossa 504 to gain access to a left side of the heart 500. This enables one or more devices of the assembly 100, such as the supporting member 130 (such as dilator 30A) and sheath 20 of the assembly 100 to be tracked over the RF guidewire 10 into the left side of the heart.

In some such embodiments, the a step of puncturing [5], is performed by first advancing the device (such as the RF guidewire 10) and tenting with the dilator 30B, as shown in FIG. 4D, to enable the RF guidewire 10 to be advanced to the puncture position, in order to the puncture the septum 502 at the fossa 504.

Using a Puncture Device for Initial Access, Positioning and Puncturing

In some such examples, as shown in FIGS. 2B-2E, the steps of accessing, positioning, and puncturing are performed using a puncture device 110.

Figure 4F:
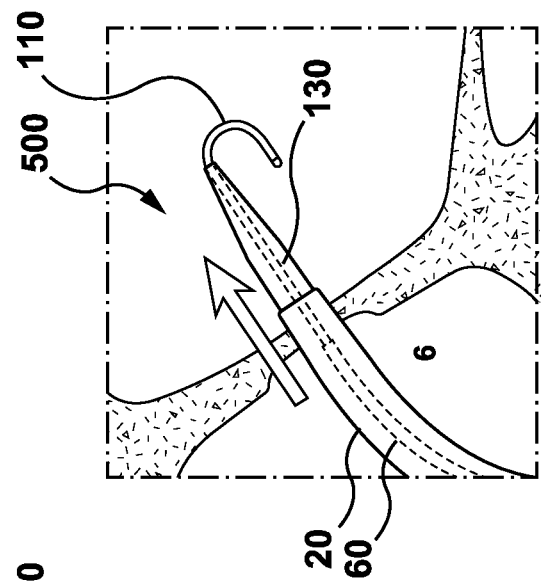
Figure 4G:
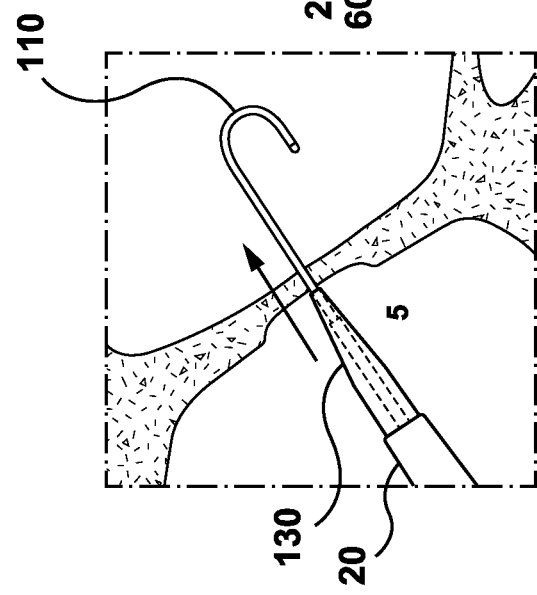

Using the Same Device for Initial Access, Positioning and Puncturing and Anchoring In accordance with an embodiment of the present invention, the method additionally comprises a step of anchoring [6], as shown in FIG. 4E, where the step of anchoring is performed using a device (such as the puncture device 110) after the step of puncturing [5] through the target tissue site, to maintain access through the target tissue site to the other side of the target tissue site, to allow one or more additional device [such as sheath 20 and the dilator 30B] to be advanced or tracked over the device (such as the puncture device 110, for example an RF guidewire 10) in order to allow crossing of the sheath 20 and dilator 30B to the other side of the target tissue site, for example into the left side of the heart, as shown in FIG. 4F, where the steps of accessing [1], positioning [4], puncturing and anchoring [5] are performed using the same device. The RF guidewire 10 may be left to maintain access to the left side of the heart as shown in FIG. 4G. The RF guidewire 10 functions as a rail to guide one more devices to the left side of the heart. In some such examples, the RF guidewire 10 provides a substantially stiff rail to guide the one or more devices to left side of the heart while being substantially atraumatic to minimize damage to the tissue.

In some such embodiments of the present invention, the step of anchoring to maintain access through the target tissue site comprises advancing the device (such as the puncture device 110) through the fossa to the left side of the heat to maintain access to the left side of the heart.

In some such examples, the step of anchoring additionally comprises removing the stylet 60 to enable anchoring by allowing the RF guidewire 10 to remain positioned to maintain access to the eft side of the heart. The sheath 20 and/or the dilator 30B may additionally be removed as well.

In some such embodiments, the steps of accessing, positioning, puncturing and anchoring are performed substantially using the wire such as the RF guidewire and the removable stylet 60.

Using a Puncture Device for Initial Access, Positioning and Puncturing

In some such embodiments of the present invention, the steps of accessing, positioning, puncturing and anchoring are performed using a puncture device (such as a wire comprising an RF guidewire 10) and a removable stylet 60

Alternatives for the Device being Used for Initial Access, Positioning and/or Puncturing—Based on the Base Claim these Dependents Depend from In some such embodiments of the present invention, the device comprises a flexible puncture device 112 where one or more of the steps of accessing, positioning, puncturing and anchoring are performed using the flexible puncture device 112. In some such examples, each of the steps of accessing, positioning, puncturing and anchoring are substantially performed using the flexible puncture device 112.

In some such embodiments of the present invention, the device comprises a substantially flexible guidewire (such as a mechanical guidewire 118 or an RF guidewire 10) where one or more of the steps of accessing, positioning, puncturing and anchoring are performed using the substantially flexible guidewire (such as a mechanical guidewire 118 or an RF guidewire 10). In some such examples, each of the steps of accessing, positioning, puncturing and anchoring are substantially performed using substantially flexible guidewire (such as a mechanical guidewire 118 or an RF guidewire 10).

In some such embodiments of the present invention, the device comprises a flexible energy based puncture device 114 where one or more of the steps of accessing, positioning, puncturing and anchoring the steps are performed using the flexible energy based puncture device 114. In some such examples, each of the steps of accessing, positioning, puncturing and anchoring are substantially performed substantially using flexible energy based puncture device 114.

In some such embodiments of the present invention, the device comprises a flexible RF guidewire and wherein one or more of the steps of accessing, positioning, puncturing and anchoring are performed using the flexible RF guidewire 10. In some such examples, each of the steps of accessing, positioning, puncturing and anchoring are substantially performed substantially using flexible the flexible RF guidewire 10.

In some such embodiments of the present invention, wherein the device comprises a flexible mechanical guidewire 118 having a relatively sharp distal tip 118d wherein one or more of the steps of accessing, positioning, puncturing and anchoring are performed using the flexible mechanical guidewire 118. In some such examples, each of the steps of accessing, positioning, puncturing and anchoring are substantially performed substantially using flexible mechanical guidewire 118.

Repeating Steps of Accessing and Positioning

In some such embodiments of the present invention, the method further comprises repeating the steps of accessing [1], shown in FIG. 4B, and positioning [4] as shown in FIG. 4D, until the device (such as the puncture device 110) is positioned at the desired target tissue site prior to the step of puncturing [5], as shown in FIG. 4E.

Reshaping the Supporting Member

In some such examples, repeating the step of positioning [4] as shown in FIG. 4D, further comprises reshaping a curvature of the supporting member 130 after removing the supporting member 130 [stylet 60], and re-tracking [3] the supporting member 130 [stylet 60] over the device, as shown in FIG. 4C (such as the puncture device 110 that has been re-positioned [1] within the SVC as shown in FIG. 4B), prior to repeating the step of positioning as shown in FIG. 4D, which in the example shown comprises a drop-down procedure to find the fossa 504. In a specific example, the supporting member 130 comprises the stylet 60, where the step of positioning is performed using the stylet 60.

In some such embodiments of the present invention, the method comprises reshaping the supporting member 130 (by pulling the stylet 60 out and re-shaping it).

Supporting Member Comprises a Stylet

In some embodiments, as discussed with respect to FIGS. 4A-4E, the step of re-shaping can be performed using the supporting member 130 comprising a stylet 60 wherein the stylet 60 is the reinforcing member 34, and the step of positioning is performed using the stylet 60.

In some such examples, the stylet element 60 can be taken out and reshaped. In other examples, the stylet element 60 along with the sheath 20 and/or dilator 30B may be pulled out and re-shaped to see what the net shape might be and then can be re-inserted therein.

Similar to embodiments described herein above, an overall method/workflow is provided that illustrates a method of carrying out a transseptal puncture procedure using an assembly 300, as described above. The method disclosed herein provides one or more advantages associated with an assembly comprising an energy delivery component that is provided separately from the rigid component. Details of the method are provided herein below.

As a general overview, in one broad embodiment, as shown in FIG. 4A-4G, a method is provided for carrying out a transsseptal puncture, the method comprising: (i) Advancing the RF wire into the superior vena cava, (ii) advancing the sheath and dilator over the wire into the superior vena cava; (iii) inserting the stylet in the dilator until it reaches a stop; (iv) withdrawing the RF wire into the stylet; (v) dropping down from the SVC into the heart to find the fossa; (vi) tenting with the dilator; (vii) advancing RF wire to puncture position; (viii) puncturing and advancing RF wire; and (ix) crossing the sheath and dilator over the RF wire; and (x) remove stylet.

More specifically, with reference again to FIG. 4A, a method is provided for carrying out a transseptal puncture procedure using an assembly 100 comprising a flexible RF wire 10 or RF guidewire 10, a sheath 20, a standard transseptal dilator 30B, and a stylet 60, the method comprises the following steps: at step 402, [1] advancing the RF wire into the superior vena cava (SVC) to gain access, as additionally illustrated in FIG. 4B. As outlined previously, in some such embodiments, providing the energy delivery component (flexible RF wire 10) separately from the reinforcing member 34, allows the energy delivery component to be used as an access wire or starter wire. More specifically, the stylet 60 defining the reinforcing member 34 can be advanced later, allowing the flexible RF wire 10 to provide access to the SVC without the use of an additional access wire. This may help reduce the number of steps and streamline the procedure, and as such may reduce procedural time and complexity.

The method additionally comprises the following steps: [2] at step 404, advancing the sheath 20 and flexible dilator 30B combination over the flexible RF wire into the SVC. As such, in this embodiment also, the flexible RF wire 10 functions as an access wire and enables the sheath 20 and dilator 30B (for example as an assembly) to be tracked over the flexible RF wire 10 into the SVC as shown in FIG. 4C. Furthermore, in one such example a standard transseptal dilator 30B may be provided without an embedded reinforcing member. This may help allow the initial track up of the sheath 20 and dilator 30B to provide a similar feel to the physician as a standard transseptal.

The method additionally provides an additional step: at step 406, [3] inserting the stylet 60 until a stop within the dilator 30B is reached. At step 408, withdrawing the RF wire into the dilator 30B and step 410, providing a step of positioning the assembly 300 by [4] performing a drop down from the SVC into the heart to locate the fossa, as shown in FIG. 4D, in order to position the assembly 300 at the target tissue site such as the fossa 504 along the septum 502 of the heart 500. The reinforcing member 34 [defined by the stylet 60] provides sufficient stiffness to the assembly 100 to facilitate the drop down. As such the reinforcing member 34 enables sufficient force transmission and torque to allow the assembly 100 to engage the septum 502, as illustrated in FIG. 4D. The method may optionally provide step 409 of using proximal markers on the RF wire to determine the relative positioning between the RF wire and the dilator/sheath. For example, the RF wire may comprise at least one proximal marker for determining whether the active tip of the RF wire is entirely within the relative positioning between the RF wire and the dilator/sheath. In one embodiment, the marker is positioned at a proximal end of the RF wire such that when the proximal marker is completely exposed from the handle/hub of the combined assembly (some combination of stylet, dilator, and sheath), the active tip of the RF wire is entirely within the lumen of the dilator/sheath. In this embodiment, when the proximal marker is no longer in view (i.e., fully within the handle/hub of the combined assembly), the active tip of the RF wire is exposed from the dilator/sheath. This allows at least for macro adjustment of the relative positioning between the RF wire and the dilator/sheath. In other embodiments, separate proximal markers may be provided to indicate the various states of relative positioning (i.e., well inside sheath/dilator, exposed from sheath/dilator, or just inside sheath/dilator). This positioning may optionally be verified or further adjusted using visualization or mapping techniques.

In one such example, having the reinforced member 34 (as defined by the stylet 60) as separate from and operable independently form the flexible RF wire 10 may additionally assist with repeatability if one or more steps in the procedure need to be repeated. If the initial placement of the flexible RF wire 10 against the septum 502 is not adequate after the drop down, the sheath 20 and dilator 30B along with the stylet 60 [and thus the reinforcing member 34] may be partially removed or partially withdrawn and the flexible RF wire 10 may be repositioned within the superior vena cava (SVC). The sheath 20, dilator 30B and the stylet 60 [and thus the reinforcing member 34] may be re-advanced over the RF wire 10 to provide adequate force transmission and torque to reposition the RF wire 10 against the septum in a drop down, as shown in FIG. 4D, to locate the fossa 504 prior to RF delivery, for example during the step of positioning the assembly 300 at the target tissue site such as the fossa 504. Thus, the reinforcing member 34 and RF wire 10 may help minimize device exchanges by reducing the need for reinserting an exchange wire. This may help reduce procedural time and enhance safety by eliminating an exchange. Thus, procedural time and risk may be reduced with the current embodiments where the energy delivery component and the rigid component are decoupled.

Furthermore, in the embodiment described herein, a removable reinforcing member is provided in that the stylet 60 and thus reinforcing member 34, is removable from and separable from the dilator 30B. By providing a removable stiffening element by way of a removable stylet 60 allows the stylet to impart different curvatures. A variable system is provided where the location of the stylet 60 within the dilator 30B may be adjusted to leverage a more preferential location for positioning against the dilator 30B against the fossa 504. Additionally the stylet 60 may be re-shapeable allowing and may be pulled out and manually reshaped. In some such embodiments, after the drop down has been performed at step 410, the physician may assess whether the angle of the stylet 60 and/or the assembly 300 is sufficient at step 412, prior to tenting. If the angle is not deemed to be sufficient, the physician may pull out the stylet 60 and reshape the curve, at step 422. The procedure then may be repeated starting at step 406 to step 412.

If the angle is deemed to be sufficient, at step 412, the method further comprises: at step 414 tenting with the dilator 30B, with reference to FIG. 4D. The reinforcing member 34 provides sufficient stiffness to the assembly 100 to enable force to be imparted to the distal end of the assembly 100, thus enabling tenting with the dilator 30B.

The method additionally comprises the step of: at step 416, advancing RF wire 10 to puncture position. As the RF wire is being advanced to the puncture position (i.e., residing outside the sheath/dilator), the user may optionally visually or tactilely monitor the proximal marker on the RF wire to determine the relative positioning between the RF wire and the dilator/sheath. In one embodiment, as the proximal marker disappears into the handle/hub of the combined assembly (i.e., some combination of stylet, dilator, and sheath), the user knows that the active tip of the RF wire is now exposed (i.e., in the puncture position). This positioning may optionally be verified or further adjusted using visualization or mapping techniques.

and at step 418 [5] puncturing and advancing RF wire 10, as shown in FIG. 4E to enable the RF wire 10 to puncture through the septum 502, at the fossa 504, to access the left side of the heart, thereby providing a step of anchoring using the RF wire 10. In some such examples, the RF wire 10 thus positioned functions as an anchor to maintain access to the left side of the heart after puncturing. The flexible RF wire 10 may provide the additional advantage of allowing the operator to push hard without injury as the flexible RF wire 10 is more flexible.

The method additionally comprises: at step 420, [6] crossing the sheath 10 and dilator 30B with the stylet 60 therein over the RF wire 10, as additionally shown in FIG. 4F. The flexible RF wire 10 may additionally protect the open end of the sheath 20/dilator 30B so it does not push hard into the tissue. At step 422, the sheath 20 and dilator 30 as well as the stylet 60 [and thus the reinforcing member 34 defined thereby] may then be removed.

As outlined herein, energy delivery component is provided as a flexible RF wire 10 that is separate from a stiff component such as a reinforcing member 34 [as provided by stylet 60], where the stylet 60 is separable from and removable from the flexible RF wire 10. This provides the additional advantage, in that the reinforcing member 34 [defined by stylet 60] may be removable after transseptal puncture and access, providing a step [7] allowing the flexible RF wire 10 to remain positioned within the left atrium which allows for immediate anchoring of the flexible RF wire 10 within the left atrium, for example as shown in FIG. 4G. In one such example, the RF wire may be positioned within the left superior pulmonary vein for anchoring. This may enable the RF wire 10 to maintain access into the left atrium, allowing removal of the stylet 60 [and thus the reinforcing member 34] to facilitate exchange of devices into the left atrium using the flexible RF wire 10. This may additionally reduce an additional exchange of the left side as it may eliminate the need for the physician to advance another wire after puncture to maintain access on the left side for tracking additional devices into the left side. As outlined above, the present embodiment also provides an additional benefit of minimizing risk of infection, embolisms and stroke by minimizing exchanges on the left side, in addition to reducing procedural time and the number of steps required.

Lockable Stylet and Flexible Puncture Device

In some embodiments of the present invention, the assembly 100 or 300 further comprises a locking feature to allow the flexible energy based puncturing device 114 (such as RF guidewire 10) to be coupled to the reinforcing member 34 (such as stylet 60) to form a needle assembly to allow the flexible energy based puncturing device 114 (such as RF guidewire 10) to be selectively usable with the reinforcing member 34, to provide feel of a needle while enabling use of an RF guidewire.

In some such examples, the locking feature may enable the puncturing device 114 and the reinforcing member 34 to be axially locked such that the puncturing device 114 and the reinforcing member 34 may be moved back and forth together. In an additional embodiment, the locking feature may additionally provide rotational locking. The locking feature allows the combination to provide the feel of a rigid RF needle while enabling the use of an RF wire 10. The combination additionally provides the advantages provided herein above of a decoupled energy delivery system where a flexible energy delivery component such as the RF wire 10 is provided separately from a supporting member 130 such as a reinforcing member 34.

In embodiments with a locking feature, the methods relating to Example 2 described above may further comprise the step of locking the reinforcing member 34 and RF wire 10 together. This may be desirable at various points in the procedure in order to provide the RF wire 10 with sufficient stiffness and pushability for a) dropping the apparatus down onto the fossa ovalis; or b) puncturing the septum.

As such, in some embodiments, the systems of the present invention provide a work flow that may reduce the number device exchanges, facilitate repeatability, provide adequate anchoring and enhance safety.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An assembly for a transseptal puncture procedure and enhancing procedural efficiency by facilitating exchange and positioning, the assembly comprising:
   a puncture device for puncturing tissue, the puncture device comprising an electrically conductive mandrel, wherein at least one proximal marker covers a proximal end of the mandrel, and at least one distal end marker which is visible under an imaging system;
   a clear or translucent layer of insulation covering the mandrel and the at least one proximal marker, the clear layer not covering the distal end of the mandrel such that the distal end of the mandrel is electrically exposed to define a distal tip electrode, wherein the diameter of the puncture device is constant at, and adjacent to, the at least one proximal marker;
   a supporting member for supporting the puncture device comprising a lumen for receiving the puncture device and a distal tip marker which is visible under the imaging system;
   wherein the puncture device is capable of being insertable within the lumen of the supporting member and being selectively usable in co-operation therewith during a portion of a procedure for puncturing tissue and wherein the puncture device is usable independently therefrom during another portion of the procedure; and wherein when the puncture device is inserted within the lumen, the at least one proximal marker allows the puncture device to be positioned relative to a proximal end of the supporting member, and the at least one distal tip marker and the at least one distal end marker allows the puncture device to be positioned relative to the supporting member by using the imaging system.

2. The assembly of claim 1, wherein the imaging system is a fluoroscopy system and the distal tip marker and distal end marker are visible under fluoroscopy.

3. The assembly of claim 1, wherein the mandrel is surrounded by an oxide coating which is covered by the clear layer of insulation, wherein the at least one proximal marker comprises a portion of the mandrel not covered by the oxide coating such that said portion defines a visible marker.

4. The assembly of claim 3, wherein the visible marker is formed by mechanical grinding of the oxide coating.

5. The assembly of claim 1, wherein the mandrel is surrounded by a polytetrafluoroethylene coating, and the at least one proximal marker comprises at least one pad printed marker on the polytetrafluoroethylene coating defining a visible marker, wherein the polytetrafluoroethylene coating and at least one pad printed marker are underneath the clear or translucent layer of insulation.

6. The assembly of claim 1, wherein at least one proximal marker comprises a pad printed marker on the mandrel defining a visible marker, wherein the pad printed marker is underneath the clear or translucent layer of insulation.

7. A transseptal puncture device for puncturing tissue and for use with a supporting member for supporting the puncture device comprising a lumen for receiving the puncture device and a distal tip marker which is visible under an imaging system, the transseptal puncture device comprising:
an electrically conductive elongate mandrel;
at least one proximal marker covers a proximal portion of the mandrel;
at least one distal end marker positioned at a distal portion of the mandrel, wherein the distal end marker is visible under an imaging system;
a clear layer of insulation covering the mandrel and the at least one proximal marker, the clear layer not covering the distal end of the mandrel such that the distal end of the mandrel is electrically exposed to define a distal tip electrode,
wherein the diameter of the puncture device is constant at, and adjacent to, the at least one proximal marker;
wherein the puncture device is capable of being insertable within the lumen of the supporting member and being selectively usable in co-operation therewith during a portion of a procedure for puncturing tissue and wherein the puncture device is usable independently therefrom during another portion of the procedure; and
wherein when the puncture device is inserted within the lumen, the at least one proximal marker allows the puncture device to be positioned relative to a proximal end of the supporting member, and the at least one distal tip marker and the at least one distal end marker allows the puncture device to be positioned relative to the supporting member by using the imaging system.

8. The transseptal puncture device of claim 7, wherein the imaging system is a fluoroscopy system and the distal tip marker and the at least one distal end marker are visible under fluoroscopy.

9. The transseptal puncture device of claim 7, wherein the mandrel is surrounded by an oxide coating which is covered by the clear layer of insulation, wherein the at least one proximal marker comprises a portion of the mandrel not covered by the oxide coating such that said portion defines a visible marker.

10. The transseptal puncture device of claim 9, wherein the visible marker is formed by mechanical grinding of the oxide coating.

11. The transseptal puncture device claim 7, wherein the mandrel is surrounded by a polytetrafluoroethylene coating, and the at least one proximal marker comprises at least one pad printed marker on the polytetrafluoroethylene coating defining a visible marker, wherein the polytetrafluoroethylene coating and at least one pad printed marker are underneath the clear or translucent layer of insulation.

12. The transseptal puncture device of claim 7, wherein the at least one proximal marker comprises a pad printed marker on the mandrel defining a visible marker, wherein the pad printed marker is underneath the clear or translucent layer of insulation.

13. A method for puncturing a target tissue with a puncture device comprising an electrically conductive mandrel, wherein at least one proximal marker covers a proximal end of the mandrel, the puncturing device further comprising a clear or translucent layer of insulation covering the mandrel and the at least one proximal maker, the clear layer not covering a distal end of the mandrel such that the distal end of the mandrel is electrically exposed to define a distal tip electrode and wherein the diameter of the puncture device is constant at, and adjacent to, the at least one proximal marker, the puncture device further comprises at least one distal end marker, the method comprising the steps of:

(i) accessing a region of tissue within a patient's body by advancing the puncture device into the region of tissue;

(ii) advancing a supporting device over the puncture device to support the puncture device, the supporting device comprising a lumen for receiving the puncture device;

(iii) positioning the puncture device relative to the proximal end of the supporting member using the proximal marker without an imaging system in a macro-positioning step;

(iv) positioning the distal end of the puncture device and a distal end of the supporting member at the target tissue site;

(v) puncturing through the target tissue site using the puncture device, wherein the supporting member supports the puncture device through the puncturing.

14. The method of claim 13, wherein step (iii) further comprises using the at least one proximal marker to determine that the distal tip of the puncture device is exposed from the distal end of the supporting device.

15. The method of claim 13, wherein step (iii) further comprises using the at least one proximal marker to determine that the distal tip of the puncture device is within the lumen of the supporting device.

16. The method of claim 13, wherein the method for puncturing tissue comprises a method for carrying out a transseptal puncture, and wherein the puncture device is a transseptal puncture device,
wherein step (i) comprises advancing the transseptal puncture device into a superior vena cava;

wherein step (iv) comprises dropping the transseptal puncture device and supporting device from the superior vena cava into a heart of the patient to locate a fossa along a septum of the heart to position the device at the fossa; and wherein the target tissue site is the fossa, such that puncturing step (v) comprises puncturing the fossa to gain access to the left side of the heart.

* * * * *